(12) United States Patent
Sohl, III et al.

(10) Patent No.: US 7,425,307 B2
(45) Date of Patent: Sep. 16, 2008

(54) ENHANCED SUBSURFACE SCANNING SYSTEM, METHOD AND COMPUTER PROGRAM PRODUCT

(75) Inventors: John H. Sohl, III, Potomac, MD (US); James Edward Tillman, Ellicott, MD (US)

(73) Assignee: Columbia Technologies, LLC, Halethorpe, MD (US)

( * ) Notice: Subject to any disclaimer, the term of this patent is extended or adjusted under 35 U.S.C. 154(b) by 10 days.

(21) Appl. No.: 10/666,558

(22) Filed: Sep. 22, 2003

(65) Prior Publication Data

US 2004/0241045 A1 Dec. 2, 2004

Related U.S. Application Data

(60) Provisional application No. 60/412,575, filed on Sep. 23, 2002.

(51) Int. Cl.
*G01N 21/00* (2006.01)
*G01N 1/00* (2006.01)
*G01N 33/24* (2006.01)
*G01V 3/15* (2006.01)
*G01V 5/00* (2006.01)

(52) U.S. Cl. ............... 422/67; 73/864.73; 73/864.74; 73/23.41; 250/253

(58) Field of Classification Search ............ 422/88–92, 422/67; 436/174; 250/288, 253; 73/864, 73/73, 864.74, 23.41, 23.35, 23, 22, 19.02, 73/1.02
See application file for complete search history.

(56) References Cited

U.S. PATENT DOCUMENTS 3,491,595 A * 1/1970 Griffeth ............ 374/142

| | | |
|---|---|---|
| 3,999,065 A | 12/1976 | Briggs |
| 4,624,194 A | 11/1986 | Zinck et al. |
| 4,725,551 A | 2/1988 | Thompson |
| 5,246,862 A | 9/1993 | Grey et al. |
| 5,283,767 A | 2/1994 | McCoy |
| 5,421,193 A | 6/1995 | Carlin et al. |

(Continued)

FOREIGN PATENT DOCUMENTS

EP 1203955 5/2002

(Continued)

OTHER PUBLICATIONS

Thoman M. Christy. 'A Permeable Memocer Sensor For The Detection of Volatile Compounds in Soil. National Ground Water Association's Outdoor Action Conference in Las Vagas, Nevada, May 1998.

*Primary Examiner*—Jill Warden
*Assistant Examiner*—Keri A Moss
(74) *Attorney, Agent, or Firm*—Venable LLP; Ralph P. Albrecht; Kyle D. Petaja

(57) ABSTRACT

An enhanced scanning solutions module is disclosed including a flow control subsystem; a detector subsystem coupled to the flow control subsystem; a dryer/moisture separator subsystem coupled to the flow control subsystem; a sampling subsystem coupled to the flow control subsystem; and a software control subsystem coupled to the flow control subsystem, the detector subsystem, the dryer/moisture separator subsystem, or the sampling subsystem. The module can include a sampling subsystem having: a sample loop; an absorbent trap; or a gas chromatography injection port. The module can further include an exhaust; a pneumatic supply; a power supply; a bypass module; a feedback signal; or a pressure control subsystem.

32 Claims, 20 Drawing Sheets

U.S. PATENT DOCUMENTS

| | | | |
|---|---|---|---|
| 5,447,055 A * | 9/1995 | Thompson et al. | 73/49.2 |
| 5,571,724 A | 11/1996 | Johnson | |
| 5,639,956 A | 6/1997 | Christy | |
| 5,687,093 A | 11/1997 | Long et al. | |
| 5,828,751 A | 10/1998 | Walker et al. | |
| 5,831,876 A | 11/1998 | Orr et al. | |
| 5,835,386 A | 11/1998 | Orr et al. | |
| 5,887,491 A * | 3/1999 | Monson et al. | 73/864.74 |
| 5,946,094 A | 8/1999 | Sahlgren et al. | |
| 5,970,804 A * | 10/1999 | Robbat, Jr. | 73/863.12 |
| 6,044,324 A | 3/2000 | Boerhave et al. | |
| 6,356,205 B1 | 3/2002 | Salvo et al. | |
| 6,405,135 B1 * | 6/2002 | Adriany et al. | 702/5 |
| 6,487,920 B1 * | 12/2002 | Robbat, Jr. | 73/863.12 |
| 6,915,211 B2 | 7/2005 | Kram et al. | |
| 6,938,506 B2 * | 9/2005 | Henry et al. | 73/866.5 |
| 7,003,405 B1 | 2/2006 | Ho | |
| 7,058,509 B2 | 6/2006 | Sohl, III et al. | |
| 2002/0043969 A1 | 4/2002 | Duncan et al. | |
| 2002/0169558 A1 | 11/2002 | Smith et al. | |
| 2004/0117117 A1 | 6/2004 | Sohl et al. | |
| 2004/0241045 A1 | 12/2004 | Sohl et al. | |
| 2004/0249654 A1 | 12/2004 | Sohl et al. | |

FOREIGN PATENT DOCUMENTS

| | | |
|---|---|---|
| EP | 1241488 | 9/2002 |
| JP | 411056101 A | 3/1999 |

* cited by examiner

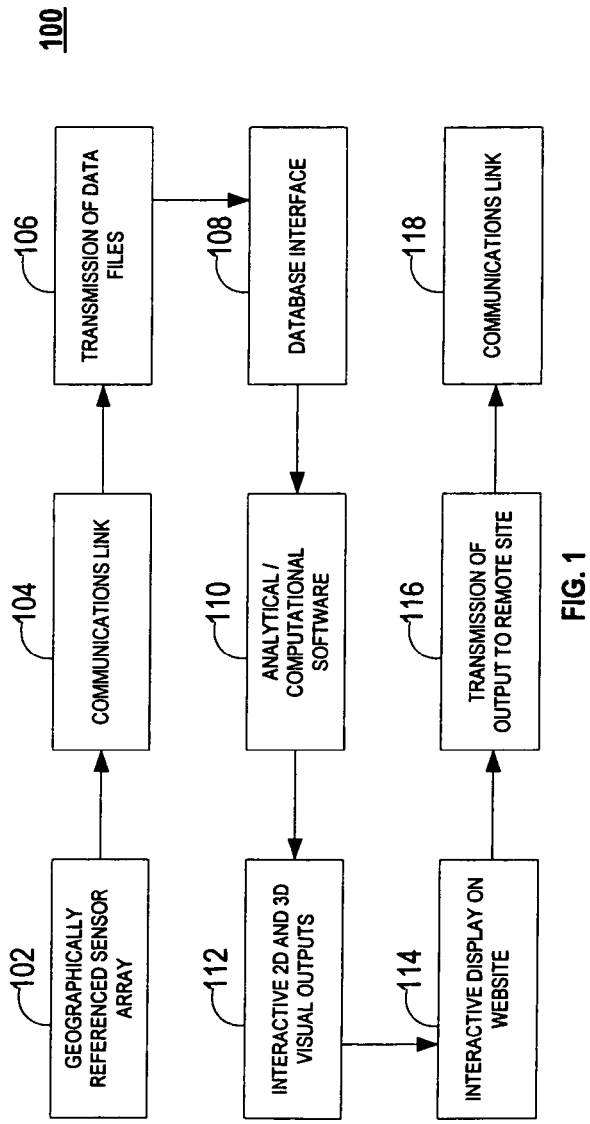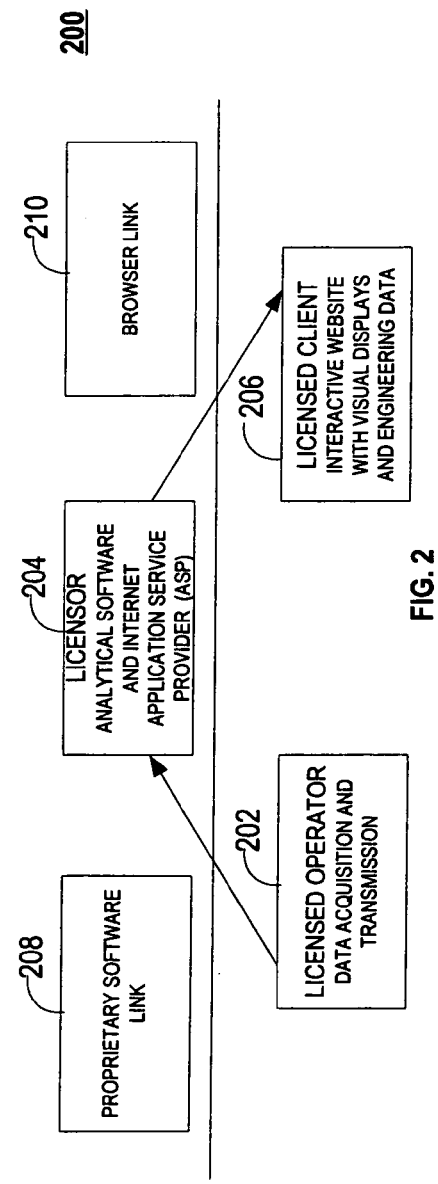

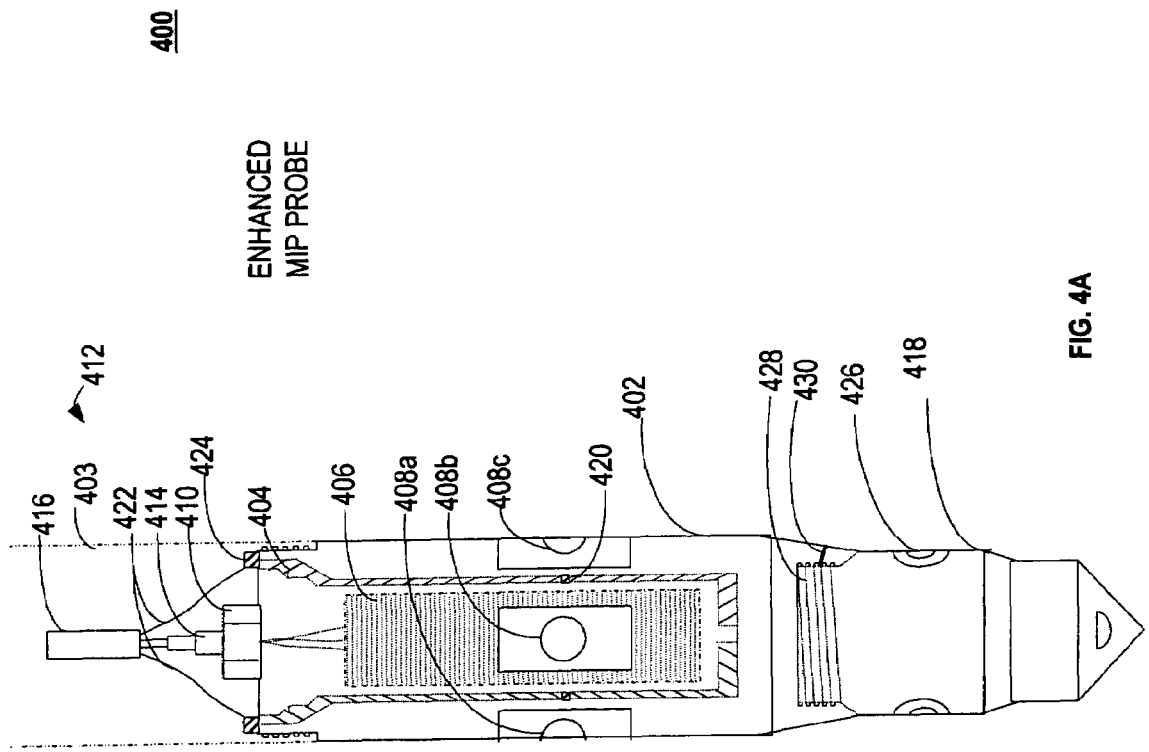

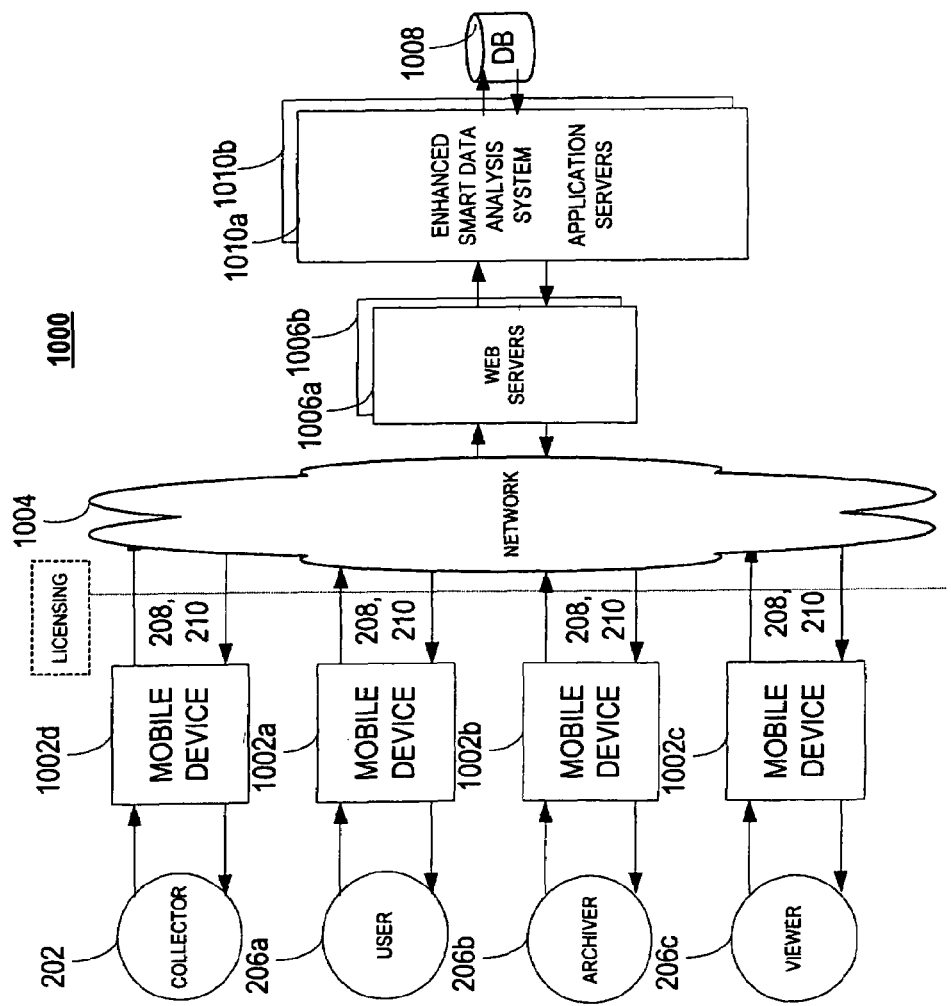
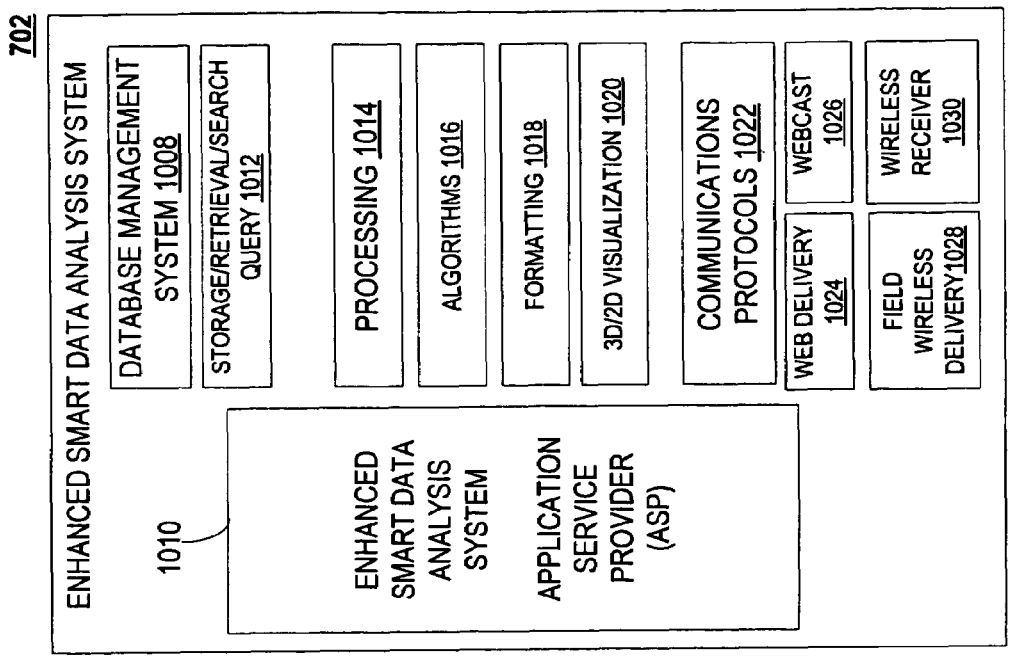
FIG. 10A
FIG. 10B

DemoCorp

Demo Corp

SmartData Solutions

Featured Projects

■ SmartData Solutions was used to delineate a source area under a manufacturing building. The resulting 3D images helped to focus remedial efforts, thereby saving time and cost. Earth Tech's client remarked, "This was the best data he had ever seen!" Dave Rosecrance of Oak Ridge, Tennessee was asked by the TDEC to present the results at their Haz Waste conference in Gatlinburg, Tennessee in May 2002.

Welcome back John Smith

Your Current Projects

PETROLEUM TERMINAL

MANUFACTURING FACILITY

Not John Smith Click here

Other Demo Corp Projects

| | |
|---|---|
| Brownfield Site | Irving Lambert - San Francisco |
| Dry Cleaner | Anna Cohen - Tampa |
| Gas Station | Vernon Wilkes - Baltimore |
| Vapor Intrusion Site | Sam Fisher - Dallas |

Assistance

Customer services
We strive to provide all our customers with the best service possible. If you are experiencing a problem, please do not hesitate to call our customer service department toll-free on 1-888-344-2704

Contact Legal Privacy

FIG. 12C

DemoCorp

Your Projects
Manufacturing Facility

SmartData Solutions

Site Information

Manufacturing Facility
Savanna, GA
Project Dates

Started: 8/12/2002

Completed: 8/21/2002
Status

Completed

Movie Information

☐ Play the movie
The Movies .AVI files contained on this CD can be viewed with Microsoft Media Player. In the event the movie does not play, you may need the appropriate decompression software.

We have enclosed this software on the CD. To install this software, simply run the file and select "Install" when prompted > Install
> Decompression
> Software
>
> Click the link above, then click "Open" to run setup program.

☐ Use another Media Player then what comes with Windows
As an alternative to Media Player, we have included a viewer called Camtasia Player that can be installed free of charge. This is in our view a very good product and should be used in case Media Player fails to play the ■ Completed Deliverables
As your order is completed, each item will be added to this screen. Your sitemap is still available by clicking on the "Sitemap" heading below.

You can get this content delivered to you on a CDROM, please contact your sales representative or the SmartData Solutions™ Team for assistance.

☐ Sitemap

☐ Images

| | | |
|---|---|---|
| ECD 1+E6, Plan View (Full site) | | 71 kb |
| ECD 1+E6, Plan View | | 71 kb |
| ECD 5+E6, Plan View | | 66 kb |
| ECD 5+E5, Transect | | 71 kb |
| ECD Slice, Lab Data | | 8 kb |

☐ Movies

Plan View, 360 Fly-around (Lab Data) — 11 mb
Plan View, 360 Fly-around (Full site) — 41 mb ☐ Presentations

SmartData Solutions™ Overview — 2 mb

Assistance

Customer services
We strive to provide all our customers with the best service possible. If you are experiencing a problem, please do not hesitate to call our customer service department toll-free on 1-888-344-2704

Webcast

View

MIP Logs

CPT01C72
PGCP101
PGCPT02
PGCPT03
PGCPT04
PGCPT05
PGCPT06
PGCPT07
PGCPT08
PGCPT08d
PGCPT09
PGCPT11
PGCPT12
PGCPT15
PGCPT18
PGCPT1CP
PGCPT23
PGCPT24
PGCPT25
PGCPT26
PGCPT27
PGCPT29

Resource

FIG. 12D

The images below were selected during the LIVE Webcast. Each Image can be selected as the basis for a movie and to be included in a report. Refer to the check boxes to the right of the image for all the options available for that image.

Previous Order Exist
A previous order exists for this webcast. You can add to this order by selecting more Deliverables and click "Update Order". To remove items from the existing order, uncheck the items and click "Update Order". Previously ordered items are listed in Red for clarity.

Oblique Views

| | | |
|---|---|---|
| SOIL | [not shown] | ☐ Include in Report |
| PID | [not shown] | ☒ Electronic Image |
| FID | [not shown] | ☐ Create Basic Movie |
| ECD | 1.0e+006 uV | |

View: Looking North (N)
Comment: lab
Click to enlarge

| | | |
|---|---|---|
| SOIL | [not shown] | ☐ Include in Report |
| PID | [not shown] | ☐ Electronic Image |
| FID | [not shown] | ☐ Create Basic Movie |
| ECD | 5.0e+005 uV | |

View: Looking West (W)
Comment: lab
Click to enlarge

| | | |
|---|---|---|
| SOIL | [not shown] | ☐ Include in Report |
| PID | [not shown] | ☒ Electronic Image |
| FID | [not shown] | ☐ Create Basic Movie |
| ECD | 5.0e+006 uV | |

View: Looking North (N)
Comment: lab
Click to enlarge

FIG. 12E

ENHANCED SUBSURFACE SCANNING SYSTEM, METHOD AND COMPUTER PROGRAM PRODUCT

CROSS-REFERENCE TO RELATED APPLICATIONS

This application is related to the following co-pending U.S. patent applications, the contents of which are incorporated herein by reference in their entireties:

U.S. Provisional Patent Application No. 60/412,575, entitled "System, Method and Computer Program for Subsurface Contamination Detection and Analysis," to Sohl, et al. filed on Sep. 23, 2002, of common assignee to the present invention;

U.S. Non-Provisional patent application Ser. No. 10/666,547, entitled "Enhanced Subsurface Membrane Interface Probe (MIP)," to Sohl, et al. filed on Sep. 22, 2003, of common assignee to the present invention;

U.S. Non-Provisional patent application Ser. No. 10/666,549, entitled "System, Method and Computer Program Product for Subsurface Contamination Detection and Analysis," to Sohl, et al. filed on Sep. 22, 2003, of common assignee to the present invention; and U.S. Non-Provisional patent application Ser. No. 10/666,557, entitled "Smart Data Subsurface Data Repository System, Method and Computer Program Product," to Sohl, et al. filed on Sep. 22, 2003, of common assignee to the present invention.

BACKGROUND OF THE INVENTION

1. Field of the Invention

The present invention relates generally to subsurface area contamination analysis systems, and more particularly to a smart data acquisition, processing and analysis tool used in the contamination area assessment and cleanup decision-making process.

2. Related Art

Large, complex environmentally impaired or contaminated sites present difficult and potentially expensive challenges for proper characterization and cleanup. Often extensive assessment efforts leave property owners and the engineering consultants with more questions than answers. Equally difficult is ascertaining the level of legal and financial liability associated with contaminated sites resulting in delays in restoring properties to economic viability. The two biggest questions being: "One, what liability does a property owner have as a result of environmental contamination?" and "Can we realistically cleanup this site within our budget?"

In today's technological climate, the availability of advanced sensors, telecommunications, computational power and visualization software has dramatically changed the way information is collected, decisions are made, and engineering systems are designed. For example, diagnostic tools such as Magnetic Resonance Imaging (MRI) coupled with intelligent databases provide radiologists and surgeons with a detailed understanding of conditions within the human body prior to invasive surgery or treatments. Furthermore, coupling real time sensors with high speed telecommunications enables medical professionals to perform surgery using robotics remotely from as far away as another continent.

The above examples are just a few among the many instances of how today's technological advances have changed the medical and scientific community. These examples also significantly change the business economics of diagnosing medical conditions and providing state of the art treatment anywhere in the world, thus leveraging the knowledge and talent of a small number of experts. A similar concept can be applied to the assessment and cleanup of environmentally contaminated or impaired properties. Simply stated, more complete and detailed information provided simultaneously to all parties involved in the assessment, risk analysis, engineering design, and decision-making process of dealing with contaminated properties, leads to making better decisions, at a decreased risk and lower cost.

Conventionally, the investigation of most environmentally contaminated sites involves an extended process including the preparation of written work plans by an environmental consultant, approval by a property owner and regulatory agencies, field investigation, laboratory analyses, and written findings of results and recommendations. This process is extremely slow (months to years) and labor intensive. The outcomes are generally subject to much questioning resulting in a repetition of the process to obtain additional information. The burden of proof placed on the property owner and the owner's environmental consultant in competition with the high cost of data acquisition results in an incomplete assessment, increased risk as a result of incomplete information, and incorrectly designed and applied cleanup tools.

The problem is compounded by the high cost of data acquisition and correlation. Most data are collected by the intrusive sampling of soil cores, groundwater, and vapor from the subsurface using drill rigs and direct push technology. These processes typically yield 5-30 samples per day for subsequent analysis by field instruments or remote fixed laboratories. In consideration of the high cost of mobilizing heavy equipment and personnel to collect the samples, budget constraints often limit the total number and amount of samples obtained, and thus the completeness of the data set for a particular site.

Furthermore, samples are typically obtained at predetermined locations and at predetermined depths specified by a presumed level of understanding on the part of the environmental consultant of the field geology. Most often, inadequate consideration is given to modifying the sampling plan based on the actual observed field conditions. These factors compound the limited data set considering any additional samples required to adequately delineate any identified contamination are not included in the current budget or work plan.

A third compounding factor in adequately assessing or characterizing property with environmental contamination using the present technology is the difficulty of effectively obtaining samples representative of the contaminant concentrations. Current soil coring and groundwater sampling devices work reasonably well in respective ideal geological regions, but are extremely ineffective in regions of complex, heterogeneous soil conditions. Typically, saturated soil regions with large grain sizes such as sand, and those highly permeable to liquids are difficult to recover using state of the art soil coring tools. In a saturated soil region with small grain sizes such as clays and silty materials, low permeability makes groundwater samples difficult to obtain. An issue in unsaturated soil conditions is that it is difficult to get a full sample recovery, to prevent the loss of volatile compounds. Again, when samples from predetermined locations and depths are not fully recovered, the data set suffers and a level of uncertainty increases. [***]

Additional elements that affect the amount and quality of information obtained during site assessments for contamination include handling and shipping errors created, transportation delays, laboratory handling errors and delays, and multiple data formats created by laboratories and various site assessment tools. Often times insufficient data is obtained to address the interaction between geology and chemical contaminant migration and degradation.

Once data is obtained the data is frequently displayed in incompatible tabular formats or two-dimensional diagrams. These difficult-to-use data formats result in delays in report preparation, review, and the decision making process. The net result is a slow process, difficult to use, and with a high level of uncertainty. The slow process becomes the basis for pricing, insuring, and engineering design resulting in expensive, delayed, and ineffective restoration of environmentally damaged property.

Therefore, given the above, what is needed is a smart data system, tools, methods and computer program product for source area contamination data acquisition, analysis and processing that allows dozens of samples to be collected and analyzed daily, producing detailed vertical profiles that can be made into transects and 3-D images of the subsurface. Further, the needed system, method and computer program product should be low-cost, rugged and accurate to produce repeatable results when operated by persons of varying degrees of knowledge and skill. The needed system should provide near real-time information useful for decision making. The desired system should aggregate collective value of data obtained on multiple sites to progressively lower the cost of restoring contaminated properties over time.

SUMMARY OF THE INVENTION

An exemplary embodiment of a system, method, and computer program product for end-to-end environmental data acquisition and delivery including the steps of: a) acquiring environmental subsurface data via direct reading sensors; b) geo-referencing the data; c) transmitting the data to a data analysis application server; and d) analyzing the data to obtain information about the data.

In an exemplary method, the data of step (a) can include: one or more data parameters.

In an exemplary method, the environmental subsurface data relates to chemical and geological attributes of the subsurface.

In an exemplary method, the direct reading sensors of step (a) can include: direct sensing technologies; optical sensors; chemical sensors; electromechanical sensors; membrane interface probe (MIP) sensors; advanced MIP sensors; laser induced fluorescence (LIF) sensors; ultraviolet induced fluorescence (UVF) sensors; polymer sensors; or haloprobe sensors.

In an exemplary method, the where the geo-referencing of the step (b) can include: geo-referencing in at least two dimensions; or geo-referencing the data to a specific point on the earth's surface.

In an exemplary method, the where the at least two dimensions can include: latitude, longitude, altitude, or time.

In an exemplary method, the where the geo-referencing of the step (b) can include: geo-referencing in at least three dimensions.

In an exemplary method, the at least three dimensions can include: latitude, longitude, altitude, or time.

In an exemplary method, the transmitting of step (c) can include: transmitting via the Internet; or transmitting via a wireless communications link.

In an exemplary method, the application server of step (c) can include: an application service provider (ASP).

In an exemplary method, the step (d) can include: storing the data in a database; mining the data; calculating the information from the data using an algorithm; performing visualization processing in at least two dimensions; displaying a graphical visualization of the data; mapping the data; or displaying in two-dimensional or three-dimensional formats the data.

In an exemplary method, the wherein the step (d) can include: refining raw data into processed data; normalizing the data for variations in acquisition of the data; normalizing for condition of a membrane of a membrane interface probe (MIP); normalizing for variation of actual subsurface conditions including at least one of chemical concentration and soil water matrix; determining relative quality efficacy data including determining at least one of: pressure, flow rate, condition of detectors, drift, calibration, depth of probe, hydrostatic, and baseline noise of analytical/electrical system; storing the data; aggregating the data into aggregate data; determining predictive modeling using the aggregate data; assessing measure of risk using the aggregate data; evaluating risk using the aggregate data; calculating total mass of chemical compounds; calculating volume of affected soil and groundwater; calculating compound identification, calculating removal costs, performing sensitivity analysis, comparing data of multiple sites.

In an exemplary method, the step of performing a sensitivity analysis can include: displaying using a "dashboard" type display; and providing results to at least one of an office device, or a field device.

In an exemplary method, the method further can include: e) posting the information on a web site for access by authorized users.

In an exemplary method, the web site can include: a secure Internet Web site.

In an exemplary method, the method can further include: e) transmitting the information over a network to a mobile device. In an exemplary method, the network can include: a wireless network.

In an exemplary method, the method further can include: e) aggregating the data into a database; f) mining the database; g) determining predictive modeling using the aggregate data; h) assessing measure of risk using the aggregate data; i) evaluating risk using the aggregate data; j) providing the user with relative analysis of various sites based on at least one of: geological information, and contaminant conditions; and k) storing the data in a database; l) grooming data; m) comparing data to at least one of: historical data, and data from other sites; n) performing datamining; or o) ranking sites.

In an exemplary method, the method further can include: e) transmitting the information including: i. transmitting the information including completed data analytics via the Internet back to source location for decision-making and process changes; or ii. transmitting the information wirelessly to a mobile device to facilitate access via Internet protocols to the information analyzed from the sensor outputs.

In an exemplary method, the method can further include: f) normalizing the data for variations in at least one of: acquisition of the data, condition of membrane of a membrane interface probe (MIP), subsurface conditions including at least one of chemical concentration and soil water matrix; or g) determining relative quality efficacy data including determining: pressure, flow rate, condition of detectors, drift, calibration, depth of probe, hydrostatic, or baseline noise of analytical/electrical system.

In another exemplary embodiment, a system, method and computer program product is set forth where the method of equipping and training licensed operators to perform sensor data acquisition at remote locations using a smart data system can include the steps of: a) charging a licensed operator a one-time setup fee to obtain a license to provide sensor data acquisition services and to obtain training; b) charging the licensed operator an ongoing subscription fee for access to and use of a smart data analysis system for transmission of data and data warehousing services; or c) charging the licensed operator an individual project fee, wherein the individual project fee varies according to the amount of analytics, display, or customer deliverables required.

In an exemplary method, the method can include transmission of the data of the step (b) can include: transmitting the data via a software link to a Web site.

In an exemplary method, the method can include the smart data analysis of the step (b) can include: using computational software including: 2D visualization or 3D visualization of geo-referenced direct reading sensor data.

In an exemplary method, the method can include the smart data analysis of the step (b) including: aggregating the data into a comparative database providing the user with relative analysis of various sites based on geological and contaminant conditions.

In an exemplary method, the data warehousing services of the step (b) can include: posting and delivering of: an interactive two-dimensional visualization; an interactive three-dimensional visualization; and engineering design data; to a Web site.

In an exemplary method, the step (c) can include: delivery of software and paper deliverables for each of the projects to at least one of: the licensed operator; or other clients with licensed access.

In another exemplary embodiment, an enhanced membrane interface probe is set forth. In an exemplary embodiment, a membrane interface probe apparatus can include: a membrane interface probe (MIP) sensor having a larger diameter than a conventional MIP sensor.

In an exemplary system, the enhanced MIP can be adapted for direct coupling to larger diameter rod systems.

In an exemplary system, the enhanced MIP can allow use of the MIP sensor with larger capacity push and hammer systems.

In an exemplary system, the enhanced MIP can allow use in situations where a low sidewall support of the drive rod string exists.

In an exemplary system, the enhanced MIP can be adapted to include two or more permeable membranes.

In an exemplary system, the enhanced MIP can include: a membrane interface probe (MIP) sensor having two or more permeable membranes.

In an exemplary system, the enhanced MIP is disclosed where the two or more permeable membranes are arranged equidistant about a circumference of the MIP sensor.

In an exemplary system, the enhanced MIP is disclosed where the MIP sensor is operative to improve circumferential sensing and to increase likelihood of collection of volatile organic mass by the MIP sensor.

In an exemplary system, the enhanced MIP is disclosed where the membrane interface probe apparatus includes a membrane interface probe (MIP) sensor adapted to improve watertight integrity by including undersea cabling electrical couplings and O-ring mechanical couplings.

In an exemplary system, the enhanced MIP is disclosed where the MIP is a modular membrane interface probe (MIP) apparatus including: a modular membrane interface probe (MIP) sensor constructed from a plurality of modular components allowing field serviceable replacement of any malfunctioning components of the plurality of modular components.

In an exemplary system, the modular MIP is disclosed including: an external barrel having a cavity; or (or throughout means and/or, i.e., a logical or operation) an inner core barrel assembly field-insertable into the cavity having a heater cavity, where the heater cavity is adapted to receive a field-insertable removable cartridge heating element.

In an exemplary system, the enhanced MIP is disclosed where the modular MIP apparatus can include a removable conductivity nose assembly.

In an exemplary system, the enhanced MIP is disclosed where the MIP apparatus includes a field-insertable removable cartridge heating element.

In an exemplary system, the enhanced MIP is disclosed where the modular MIP apparatus can include a waterproof electrical connector and/or an o-ring seal.

In an exemplary system, the enhanced MIP is disclosed where the membrane interface probe apparatus can include: a membrane interface probe (MIP) sensor including a removable trap directly into the probe for the collection and concentration of volatile organic compounds.

In an exemplary system, the enhanced MIP is disclosed where the removable trap enables detection of lower levels of concentration of the volatile organic compound, and specific identification of compounds through post run chromatographic analysis.

In an exemplary system, the enhanced MIP is disclosed where the MIP further can include: providing for calibration of the MIP sensor using chromatographic methods.

In an exemplary system, the enhanced MIP is disclosed where the MIP can further include means for simultaneous trapping and concentrating of volatile organic compounds during MIP sampling and logging events.

In an exemplary system, the enhanced MIP is disclosed where a membrane interface probe apparatus can include: a membrane interface probe (MIP) sensor including a heated transfer line from a body of the MIP sensor to a surface detector suite minimizing loss of volatile organic compounds in a cold transfer line.

In an exemplary system, the enhanced MIP is disclosed where a membrane interface probe apparatus can include: a membrane interface probe (MIP) sensor including an enhanced scanning solutions module, and a sample introduction system adapted to reduce overall equipment footprint and cost; to introduce calibration gases; and to allow for simultaneous sampling of volatile organic gas stream for immediate chromatographic analysis.

In an exemplary system, the enhanced MIP is disclosed where a membrane interface probe apparatus can include: a membrane interface probe (MIP) sensor including a global positioning system (GPS) receiver integrated with a data acquisition system adapted to allow simultaneous geo-referencing of sampling points with sample data.

In an exemplary system, the enhanced MIP is disclosed where a membrane interface probe system can include: a membrane interface probe (MIP) sensor including a mobile device in wireless communication with a data acquisition system enabling near real-time transfer of data from the MIP sensor to a base station.

In an exemplary system, the enhanced MIP is disclosed where the mobile device can include a graphical display and control module adapted to operate the data acquisition system operation.

In an exemplary system, the enhanced MIP is disclosed where the mobile device is portable.

In an exemplary system, an enhanced scanning solutions module is disclosed including a flow control subsystem; a detector subsystem coupled to the flow control subsystem; a dryer/moisture separator subsystem coupled to the flow control subsystem; a sampling subsystem coupled to the flow control subsystem; a software control subsystem coupled to the flow control subsystem, the detector subsystem, the dryer/moisture separator subsystem, or the sampling subsystem.

In an exemplary system, an enhanced scanning solutions module is disclosed where the sampling subsystem can include: a sample loop; an absorbent trap; and a gas chromatography injection port.

In an exemplary system, an enhanced scanning solutions module is disclosed where the module further include an exhaust; a pneumatic supply; a power supply; a bypass module; a feedback signal; or a pressure control subsystem.

In another exemplary system, an enhanced scanning solutions module is disclosed where the enhanced scanning solutions module can include: a detector subsystem; a sampling subsystem; a software control subsystem coupled to the detector subsystem, and the sampling subsystem.

In an exemplary system, the enhanced scanning solutions module further includes a dryer/moisture separator subsystem coupled to the software control subsystem.

In an exemplary system, the enhanced scanning solutions module can include the sampling subsystem including: a sample loop; an absorbent trap; a gas chromatography injection port.

In an exemplary system, the enhanced scanning solutions module further includes: an exhaust; a pneumatic supply; a power supply; a bypass module; a feedback signal; or pressure control subsystem.

In an exemplary system, the enhanced scanning solutions module can include on-the-fly reconfigurability, and can further include: a plurality of operator-selectable modes.

In an exemplary system, the enhanced scanning solutions module can further include: a plurality of pre-programmable operating modes that interactively reconfigures to perform any of a plurality of functions, subject to particular conditions.

In an exemplary system, the enhanced scanning solutions module can further include: an interface between the detector subsystem and a gas handling subsystem allowing insertion of: a sample, another detector, a flowpath, a flow path rate, a dryer, an exhaust, a feedback, or a trap.

In an exemplary system, the enhanced scanning solutions module, the software control subsystem can include: a data logger; a sequencer; a valve control system; a monitor; a display; or a recording function.

Further features and advantages of the present invention, as well as the structure and operation of various embodiments of the present invention, are described in detail below with reference to the accompanying drawings.

BRIEF DESCRIPTION OF THE DRAWINGS

Various exemplary features and advantages of the invention will be apparent from the following, more particular description of exemplary embodiments of the present invention, as illustrated in the accompanying drawings wherein like reference numbers generally indicate identical, functionally similar, and/or structurally similar elements. The left most digits in the corresponding reference number indicate the drawing in which an element first appears.

FIG. 1 depicts an exemplary embodiment of a block diagram illustrating an environmental data acquisition and delivery process according to an exemplary embodiment of the present invention;

FIG. 2 depicts an exemplary embodiment of a block diagram illustrating a business process according to an exemplary embodiment of the present invention;

FIG. 4A depicts an exemplary embodiment of a high level schematic diagram illustrating a membrane interface probe (MIP) significantly redesigned according to an exemplary embodiment of the present invention;

FIG. 10A depicts an exemplary embodiment of a system hardware architecture providing an exemplary enhanced smart data analysis client-server system according to the present invention;

FIG. 10B depicts an exemplary embodiment of an application service provider (ASP) embodiment of an exemplary embodiment of the enhanced smart data analysis system including exemplary subsystem modules according to the present invention;

FIG. 12C depicts a graphical user interface of a browser illustrating an exemplary embodiment of a web logon window of a Demo Corporation providing access to the Smart database system according to the present invention;

FIG. 12D depicts a graphical user interface of a browser illustrating an exemplary embodiment of a web window depicting exemplary deliverables for a Manufacturing Facility of a Demo Corporation providing access to graphical renderings on the Smart database system according to the present invention; and FIG. 12E depicts a graphical user interface of a browser illustrating an exemplary embodiment of a browser window depicting exemplary selectable deliverables according to the present invention.

DESCRIPTION OF AN EXEMPLARY EMBODIMENT OF THE INVENTION

Figure 3:
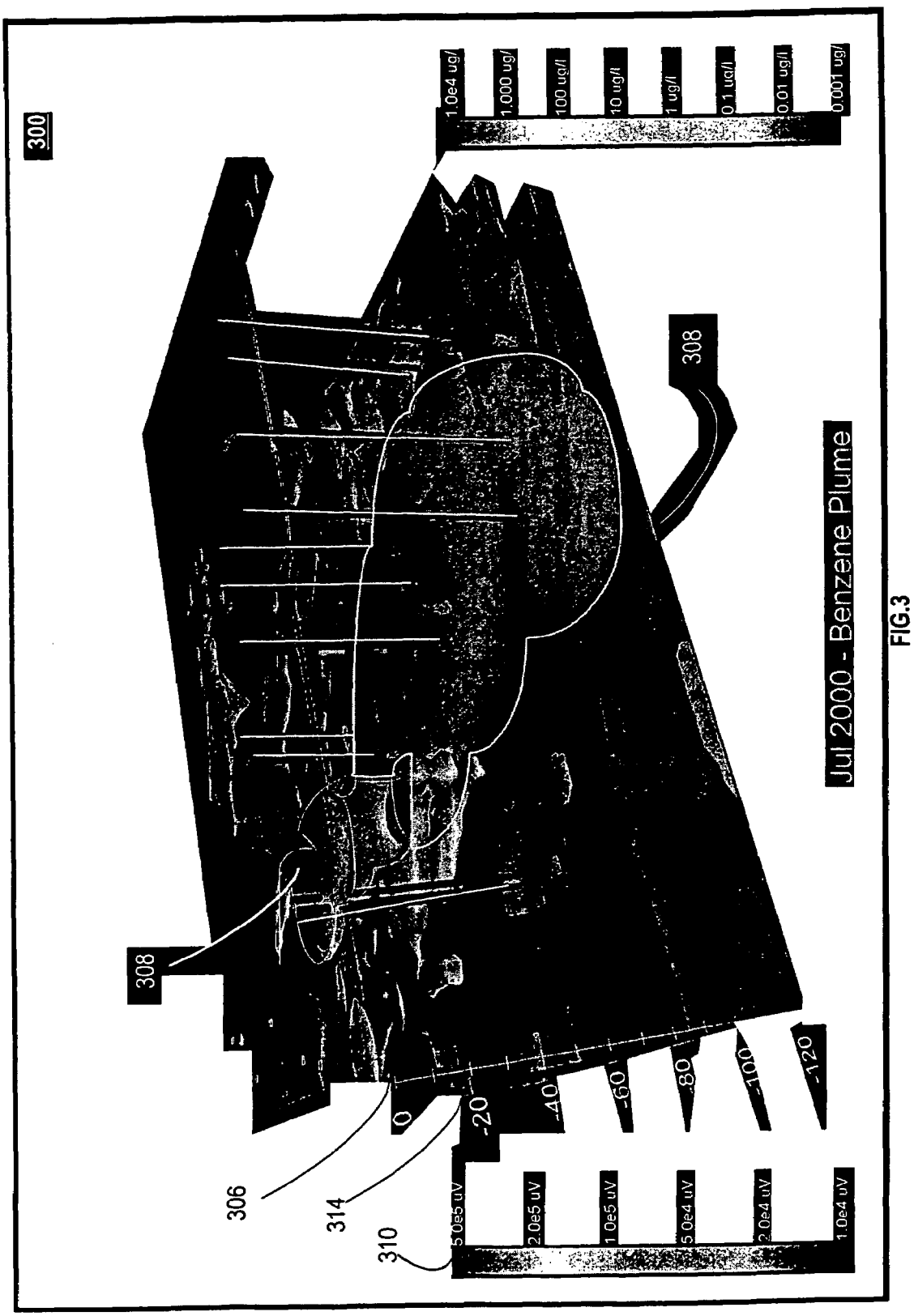
FIG. 3 depicts an exemplary embodiment of an exemplary window or screen shot, generated by a graphical user interface (GUI) of the present invention, showing a remediation foot print of a site.

A preferred exemplary embodiment of the invention is discussed in detail below. While specific exemplary embodiments are discussed, it should be understood that this is done for illustration purposes only. A person skilled in the relevant art will recognize that other components and configurations can be used without parting from the spirit and scope of the invention. The present invention meets the above-identified needs by providing a system, method and computer program product for source area contamination data acquisition, analysis and processing.

The method and computer program product of the present invention allow clients to reap the benefits of recent advances in sensor technology, rapid computational analysis and wireless data delivery to more quickly and reliably: create a diagnostic image of the hydrogeology and contamination under a site, assess the transaction and health risks of a property, avoid downstream costs, and complete a transaction or close files on a site in a shorter amount of time than conventionally possible. The smart data process is capable of collecting far more data per day than conventional approaches, provides data in near real-time that can be used to make timely decisions, and provides the data in easy-to-use formats.

In an exemplary embodiment, the smart data system is utilized to expedite the reliable characterization of the subsurface. Site assessments can be more effectively accomplished because the smart data produced by the present invention are of higher resolution so fewer interpretive mistakes will be made, are available immediately, and can be processed and mapped on a daily basis. Thus, results can be used to direct the next day's activities. The smart data system according to an exemplary embodiment of the present invention can also dramatically reduce the costs of remediation because the system provides a more focused picture of the chemical occurrences relative to site hydrogeology.

In an exemplary embodiment, the smart data system includes a database for storing aggregate data collected from multiple sites. In an exemplary embodiment, the smart data system takes raw data, accumulates data from the MIP system, from gas chromatographic analysis, from geographic position, from other sensors, and other data sets. The smart data system can process raw data to refine the data, can normalize for variations in acquisition, and can perform quality assurance analysis on the data.

The processing to normalize for variations can, e.g., compensate for drift in performance or condition of the membrane, and for variations actual subsurface conditions such as, e.g., chemical concentration, and the soil water matrix. Processing can include analysis of the relative quality and efficacy of the data. The processing system can analyze and account for variations in pressure, flow rate, condition of detectors (can account for drift and can calibrate, e.g., using a tracer gas), depth of the probe (hydrostatic), and in the baseline noise due to the analytical/electrical system.

The data can be mined and processed including, e.g., use of 3D visualization technology, and can be delivered in near real-time to the field for access by field personnel via, e.g., an application service provider (ASP), a web-based interface, and wireless device access. Video can be used to illustrate changes over time.

Data can be aggregated from multiple sites, and can be used as a predictive measure of risk and performance.

I. Overview

The present invention provides a system, method and computer program product for source area contamination data acquisition, analysis and processing.

Organizations including property owners, lending institutions, insurance underwriters, and consulting engineers—see lower costs, shorter project cycle times, and an acceleration of regulatory and financial underwriting approvals.

As mentioned above, traditional environmental investigation and cleanup economics have been driven by the high cost and delays of data acquisition. This leads to poorly designed and expensive engineering approaches and ineffective cleanup. The smart data tool of the present invention provides ten to a hundred times more data at a fraction of the time and costs. More critically, smart data analysis, presentation and reporting services turn this data into high-impact, decision oriented information with a net benefit of 30-50% lower cost for the property owners and a better quality outcome, more quickly.

The present invention provides multiple levels of value creation:

Property Owners—lower cost of investigation and cleanup, faster cycle time, & lower insurance costs;

Consulting Engineers—10 to 100 times more data which results in more effective cleanup at lower cost;

Insurance Underwriters—more detailed information which results in less uncertainty and risk;

Service Partners—significant increase in sales at higher margin; and

Strategic Sponsors—access to a large number of highly qualified service providers of cutting-edge technology.

In addition, the present invention's approach substantially lowers the uncertainty associated with environmental characteristics of a property. This, in turn, accelerates property transactions and lowers the premiums for environmental insurance. Research into this market driver indicates that 40 to 60% of environmental insurance premiums and escrow requirements stem from uncertainty in the environmental assessment. The smart data provides a comprehensive quantification and easily understood 3-D representation of the environmental conditions (see FIG. 3), which substantially increases the clarity and visibility of potential problems, improves decisions, and lowers risk.

The present invention is now described in more detail herein in terms of the above examples. This is for convenience only and is not intended to limit the application of the present invention. In fact, after reading the following description, it will be apparent to one skilled in the relevant art(s) how to implement the following invention in alternative embodiments. For example, the present invention can be used for the in-site performance monitoring of remediation of volatile organic compounds by combining in-situ sensors, geo-referenced positioning, wireless transfer of data to a base station, transfer of data via the Internet, computational software, and display on an interactive web site.

The present invention can also be used to acquire large amounts of geo-referenced data on the chemical and physical parameters of inland water bodies. This data can in turn be used to monitor biological ecosystems, environmental contamination, and compliance with discharge requirements for ships and vessels.

II. System Operation

A. Process

The method and computer program product of the present invention employs a unique end-to-end process of environmental data acquisition and delivery as illustrated in FIG. 1. FIG. 1 depicts in an exemplary embodiment, an exemplary process in which one or more of the following steps can be performed:

1. Acquisition of data parameters using direct reading sensors in-situ.

2. Geo-referencing each data parameter to a specific point on the earth's surface so as to generate a geographically referenced sensor array as shown in step 102.

3. Transmission of the data parameters via, e.g., one or more communications network link such as, e.g., wireless communication link as shown in step 104, and transmission over a network such as, e.g., the Internet as shown in step 106 to a database at, e.g., an Application Service Provider (ASP), for analysis and display, making use of communications links and storage for later access and query in a database via a database interface as shown in step 108.

Performance of data analytics and processing including calculations, visualization in graphic formats, mapping, and display in two-dimensional and three-dimensional formats, making use of analytical/computational software as shown in step 110, and creating interactive 2D, 3D, and n-D (such as, e.g., time-lapsed video) visual outputs as shown in step 112. Additional calculations can also include, e.g., total mass of chemical compounds, volume of affected soil and groundwater, compound identification, removal costs, and/or sensitivity analysis using a "dashboard" type display. In an exemplary embodiment, the smart data system can include a database for storing raw data, analyzed data, and aggregate data collected from multiple sites. The reader is referred to, e.g., FIGS. 1, 8B, 10B, and 12A, for a more detailed discussion regarding the smart data system according to the present invention. In an exemplary embodiment, the smart data system can take raw data, such as, e.g., accumulating data from the MIP system, from gas chromatographic analysis, from geographic position, from other sensors, and from other data sets. The smart data system can process raw data to refine the data, can normalize for variations in acquisition, and can perform quality assurance analysis on the data. The processing to normalize for variations can, e.g., compensate for drift in performance or condition of the membrane, and for variations actual subsurface conditions such as, e.g., chemical concentration, and the soil water matrix. Processing can include analysis of the relative quality and efficacy of the data. The processing system can analyze and account for variations in pressure, flow rate, condition of detectors (can account for drift and can calibrate, e.g., using a tracer gas), depth of the probe (hydrostatic), and in the baseline noise due to the analytical/electrical system. The data can be mined and processed including, e.g., use of 3D visualization technology from step 112, and can be delivered in steps 114, 116, 118 in near real-time to the field for access by field personnel via, e.g., an application service provider (ASP), a web-based browser interface, and a wired or wireless communication device access. Video can be used to illustrate changes over time.

4. The aggregation of data into a comparative database, making use of the database interface as shown in step 108, and providing the user with relative analysis of various sites based on geological and contaminant conditions, including interactive display as shown in step 114. Data can be aggregated from multiple sites, and can be used as a predictive measure of risk and performance.

5. Posting of the completed data analytics for interactive access via, e.g., a secure Internet Web site, and for viewing by approved individuals, can be provided as also shown in step 114.

6. Transmissions of the completed data analytics via, e.g., the Internet, back to the source location for decision-making and process changes, can be provided as shown in step 116.

7. The use of wireless communication devices to facilitate connection of the sensor outputs to the Internet can be provided in an exemplary embodiment as shown in steps 104, 118. Of course a wired communications link can be used to the extent that such a link is available.

B. Business Process

In an exemplary embodiment, an entity may utilize a business process to implement and offer for sale services utilizing the smart data system, method and computer program product of the present invention. An exemplary embodiment of this business process is illustrated in FIG. 2 including performing one or more of the following steps:

1. Equipping and training licensed operators ("users") 202 to perform sensor data acquisition at remote locations using the smart data system. These operators, in an exemplary embodiment, can pay a one-time setup to obtain a license and training; an ongoing subscription fee for access to the present invention's analytical software and data warehousing services; and/or individual project fees, which can vary according to the amount of analytics, display, and customer deliverables required. The licensed operators 202 can provide data acquisition and transmission services for a fee, or for a share in revenues.

2. Transmission of the data through a software link to a Web site operated by the entity can be provided as shown using a proprietary software link 208, in an exemplary embodiment.

3. Data analysis by the entity using computational software according to the methodology of the present invention can be performed as shown by licensor 204. In an exemplary embodiment, the data can be analyzed using analytical software. In another exemplary embodiment, an application service provider (ASP) model may be employed as shown, and as discussed further below, with reference to FIG. 10B. The services of the ASP can be used in exchange for a fee paid to the ASP, in an exemplary embodiment. The fee can be a one time fee, a periodic fee, a bundled fee, and/or a subscription fee.

4. The aggregation of data into a comparative database such as, e.g., the Columbia Technologies' Environmental Comparables Knowledgebase (ECK) available from Columbia Technologies, LLC of Halethorpe, Md., U.S.A., providing the user with relative analysis of various sites based on geological and contaminant conditions can be performed by licensor 204.

5. Posting and delivery of interactive two-dimensional and three-dimensional visualizations (such as, e.g., those shown in FIG. 3 in 3D visualization 300 having one dimension in the x-direction represented by x-axis 308, another dimension in the y-direction represented by y-axis 314, another dimension in the z-direction represented by z-axis 306) and key engineering design data to an interactive Web site 206 can be operated by the entity and can be performed by licensor 204. The visualizations and data can be accessed via a browser as shown in 210 using, e.g., an Internet browser, and/or a hyper text markup language (HTML) link, for example. The visualizations can include, e.g., as shown in FIG. 3, geo-referenced locations on a 3D spatial map indicating from where the MIP probe samples were obtained. Color-coding may be employed as indicated in color band indicator 310. Geographic information system renderings, trans-sections, 360 degree fly-around movies, volumetric calculations, 3Dsurface area contour mapping, 3D videos of a contaminant plume vs. a ground water(GW) well, graphical comparisons of a GW samples to continuous sensor profile may be employed as methods of displaying the data.

6. Delivery of software, visual displays, engineering data, and paper deliverables for each project to licensed clients 206 and/or other clients with licensed access.

C. Enhanced Membrane Interface Probe (MIP)

Figure 8A:
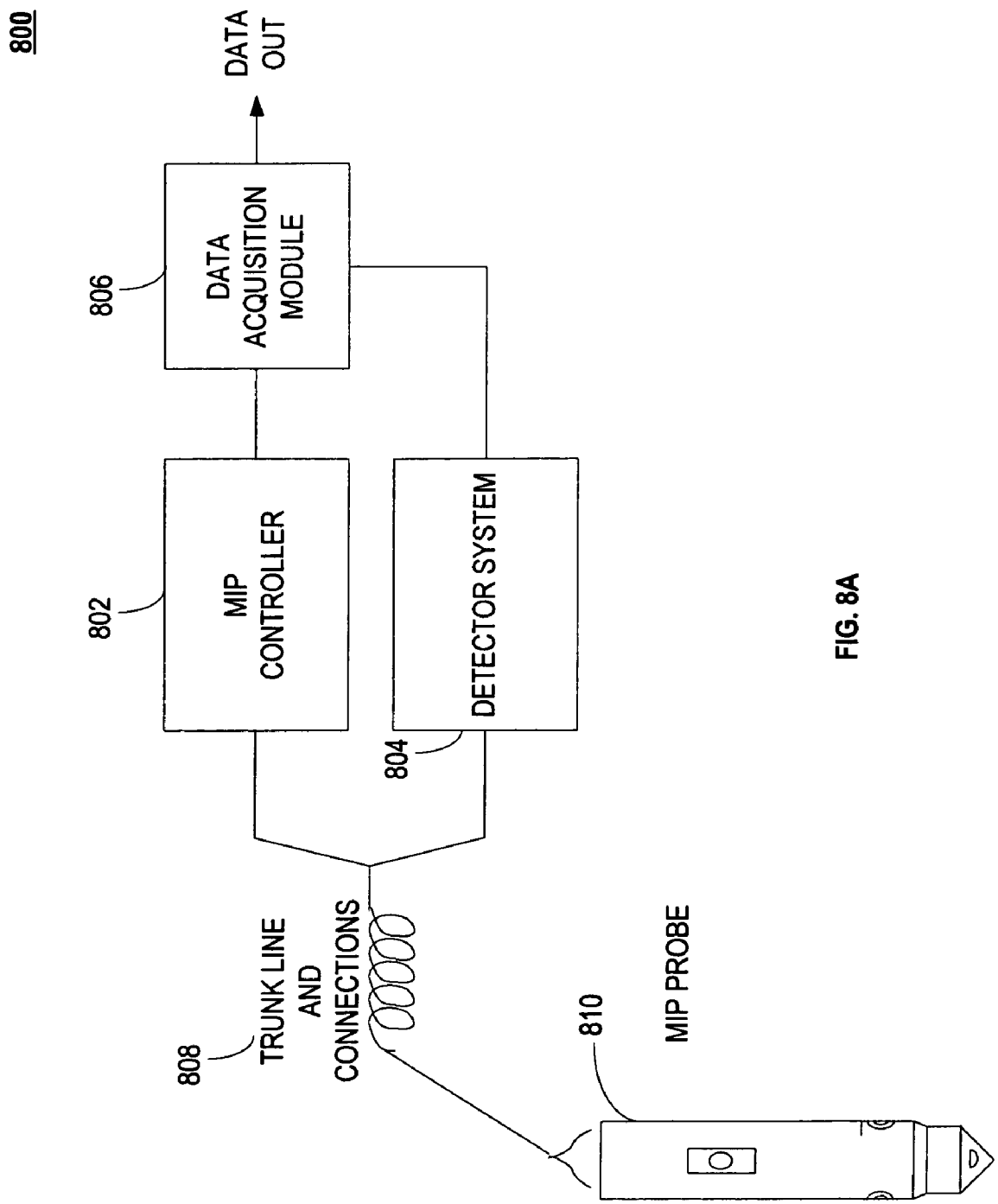
FIG. 8A depicts an exemplary embodiment of a MIP system including a MIP probe, a controller, a detector and a data acquisition module according to the present invention.

In an exemplary embodiment of the present invention, a Membrane Interface Probe (MIP) 810, shown in FIG. 8A, available from GEOPROBE SYSTEMS, INC. of Salina, Kans., USA and described in U.S. Pat. No. 5,639,956, (the '956 patent) the contents of which are incorporated herein by reference in its entirety, can be used as part of the smart data system to transport volatile organic compounds from the geological subsurface to the surface for measurement using chemical detectors. An exemplary embodiment of an improved MIP 400 is described below with reference to FIGS. 4A-4D. The MIP described in the '956 patent can include a dipole electrical conductivity sensor 426 for the measurement of conductivity in-situ as an indicator of soil grain size. The probe may be driven or hammered into the geological subsurface using hydraulic or pneumatic reaction weight or hammers.

FIG. 4A depicts, in an exemplary embodiment of the present invention, a MIP 400 enhanced to include a number of useful features. Of course, in alternative exemplary embodiments of the present invention, MIP 400 can be modified to include any combination of a number of useful features outlined below. For example, in an exemplary embodiment of the present invention, the MIP 400 can be significantly redesigned and enhanced to incorporate one or more of the following advantageous features as depicted in FIG. 4A.

1. In an exemplary embodiment, the enhanced MIP 400 can include an outer barrel assembly 402, which can include a larger diameter probe (2.125-inches) as illustrated in diagram 400 of FIG. 4 than conventionally available for direct coupling to larger diameter rods 403. The large diameter rods 403 can significantly increase the yield strength of the drive rod string allowing for the rods' use with stronger push/hammer systems and in situations where there is low sidewall support of the drive rod string.

2. In an exemplary embodiment, the enhanced MIP probe 400 can be redesigned in a modularized in removable, multi-subsystem, field-replaceable fashion as shown in 4A-4D. As shown, MIP 400 can include the external barrel assembly 402 depicted in detail in FIG. 4D, including a cavity into which can be tightly coupled an inner core barrel assembly 404, which is depicted in greater detail in FIG. 4C. The inner core barrel assembly 404 can be fashioned to receive a field replaceable cartridge heater element 406. The heater 406 is used to heat the zone around membranes 408, described further below. MIP 400 is also enhanced to include various external watertight connections 412. Watertight connections 412 include various components taken from underwater cabling applications. The watertight connections 412 include bulkhead electrical connector 410, inline electrical connector 414 and splice 416. Bulkhead electrical connector 410 can be a SEA CON LSG-6-BC-HP, and inline electrical connector 414 can be a SEA CON RMG-6-FS inline connector, both available from SEA CON Brantner & Associates Inc., of San Diego, Calif. USA. Also shown are external vapor connections, including gas vapor subassembly 422 and inlet and outlet gas ferrell connections 424. The MIP 400 is enhanced to include a removable conductivity probe nose assembly 418 having dipoles 426 and thread 428 as well as cap screws 430 holding the nose assembly 418 in place when coupled to the outer barrel assembly 402. Diagram 460 of FIG. 4D includes a detailed level schematic diagram illustrating an exemplary external barrel assembly lengthwise cross-section (top), side cross-section A-A (middle left) of an exemplary three permeable membrane embodiment, a sector cross-section of an o-ring port at an exemplary permeable membrane (detail A), and a exterior view of an exemplary permeable membrane (bottom middle) and detail B, of enhanced MIP 400.

Figure 4B:
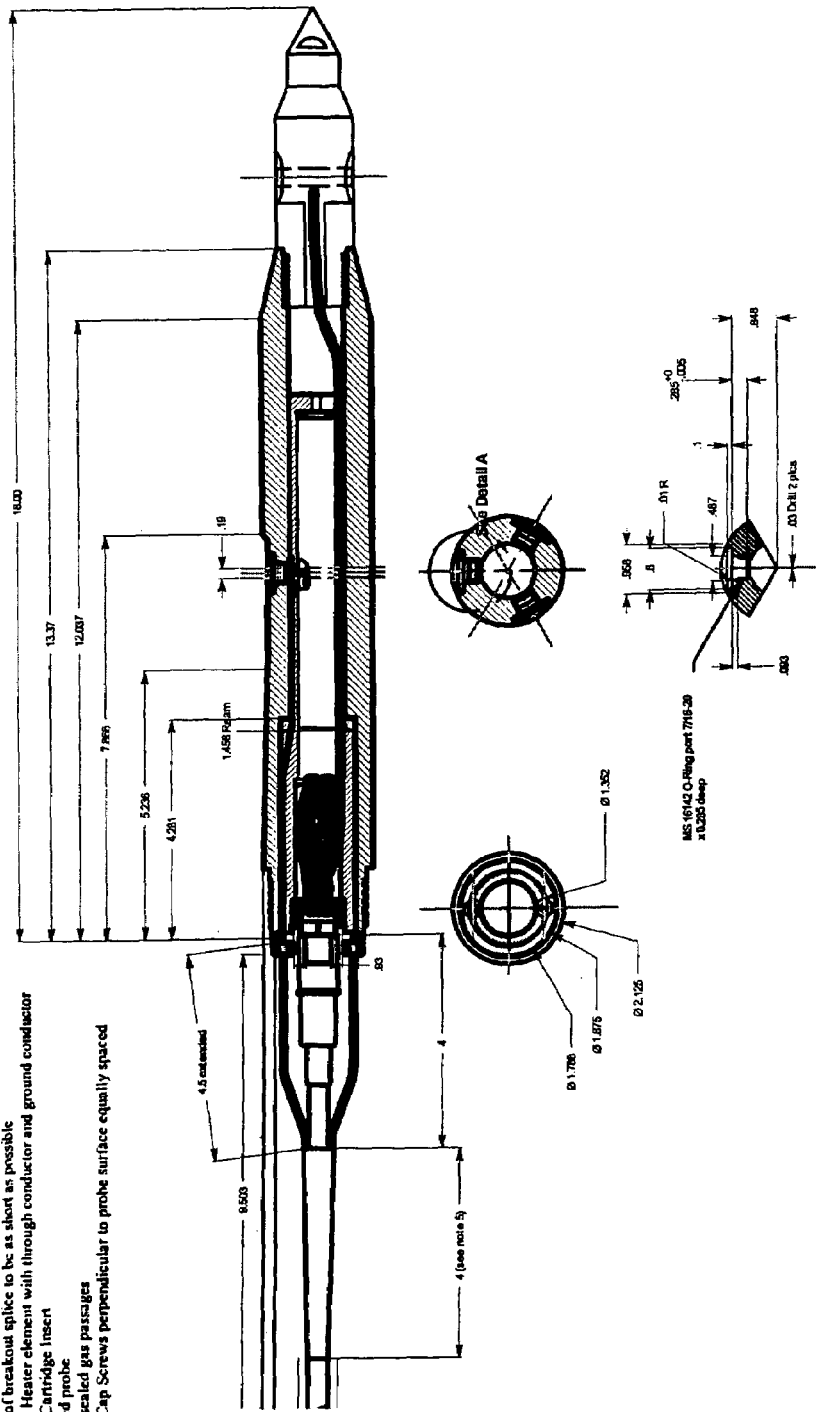
FIG. 4B depicts an exemplary embodiment of a detailed level schematic diagram illustrating a membrane interface probe (MIP) significantly redesigned according to an exemplary embodiment of the present invention, having a cross-sectional view of an exemplary modular MIP including two cross-sections and a sector cross-section.
Figure 4C:
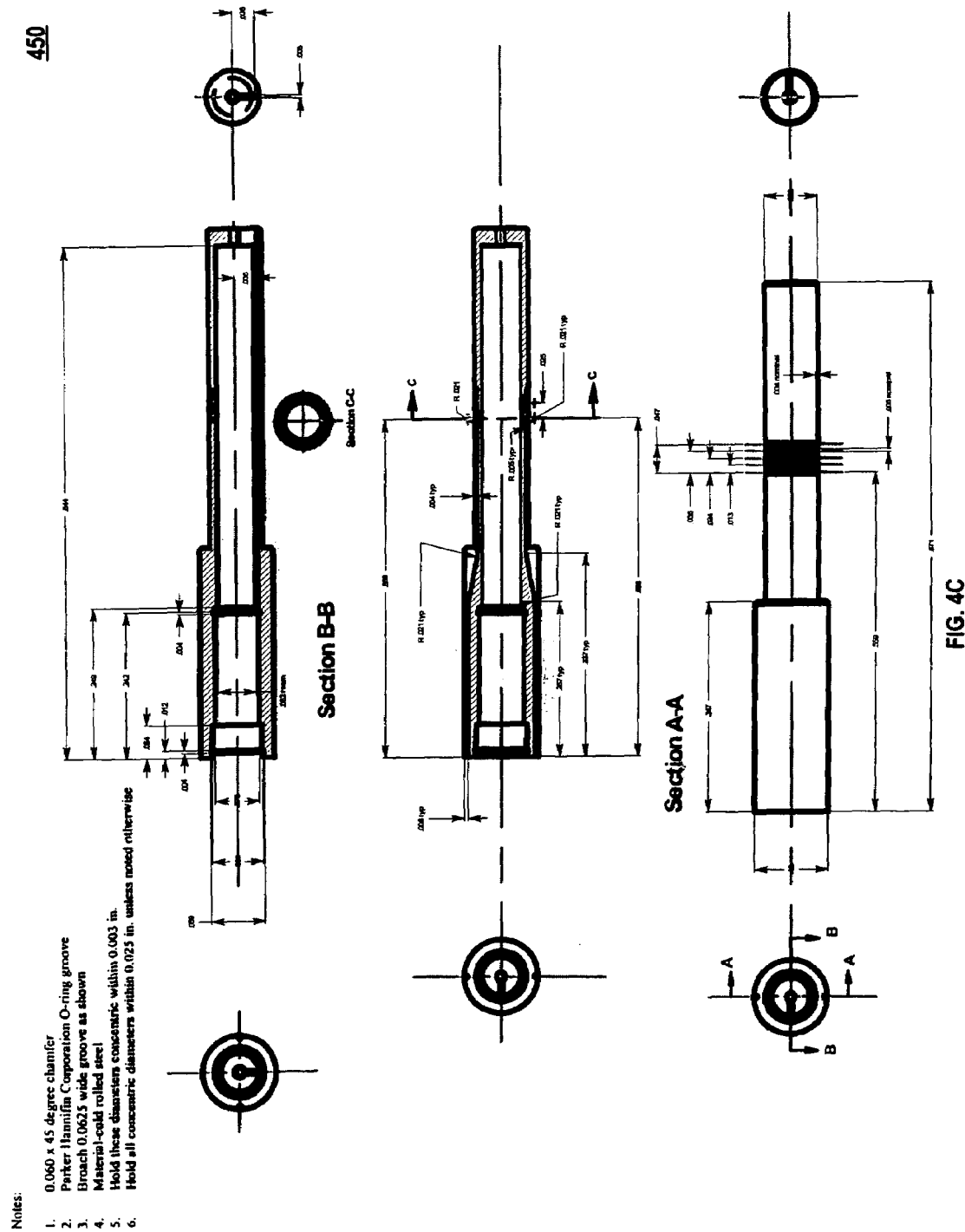
FIG. 4C depicts an exemplary embodiment of a detailed level schematic diagram illustrating a membrane interface probe (MIP) significantly redesigned, and illustrating an inner core barrel assembly having O-Ring grooves, according to an exemplary embodiment of the present invention.
Figure 4D:
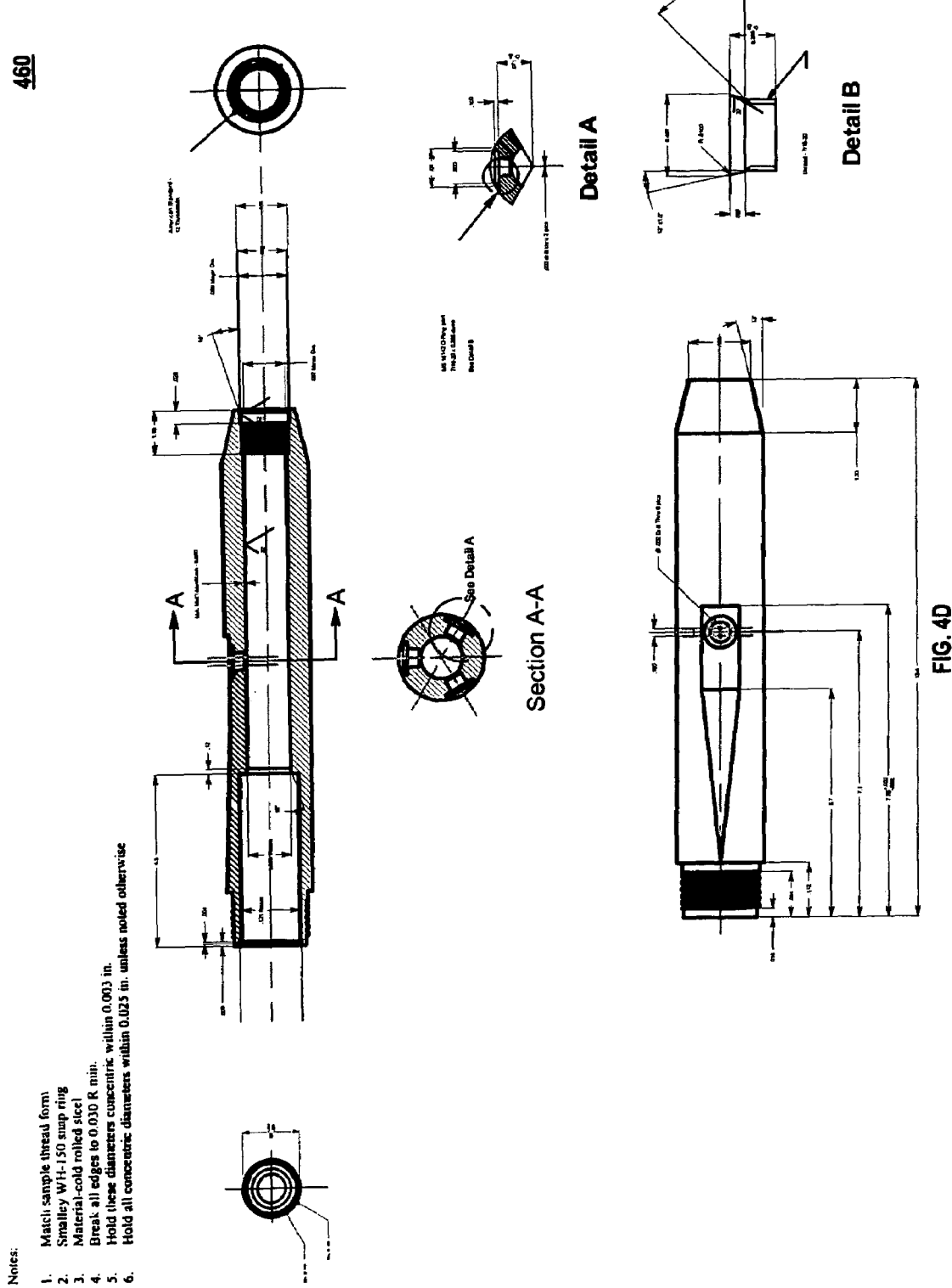
FIG. 4D depicts an exemplary embodiment of a detailed level schematic diagram illustrating an exemplary external barrel assembly of an enhanced membrane interface probe (MIP) significantly redesigned according to an exemplary embodiment of the present invention.

3. In an exemplary embodiment, the enhanced MIP 400 can include an increased number (two or more) of permeable membranes 408 as compared to conventional MIP probes such as the single permeable membrane 408 shown in the '956 patent. As illustrated in the exemplary embodiment of FIG. 4A, two or more permeable membranes 408, such as, e.g., three (408a, 408b, 408c as shown in FIGS. 4A and 4B) to provide for greater circumferential sensing and the potential for double, triple, or more times as much volatile organic mass to be collected by the probe 402 in each given time period. In the exemplary embodiment depicted in FIG. 4B, permeable membranes 408a, 408b, and 408c can provide improved circumferential coverage than conventional versions of MIP probes 400. Diagram 440 of FIG. 4B illustrates and exemplary embodiment including exemplary manufacturing tolerances and a cross-section of the enhanced MIP probe 400. Diagram 440, in an exemplary embodiment includes two cross-sections illustrating exemplary vapor connecting ports (on the left middle) and an exemplary tri-permeable membrane embodiment (labeled site detail A, on the right middle) of the present invention, and a sector cross-section illustrating an exemplary O-ring port (labeled Detail A) and single permeable membrane. This increase in mass flow can significantly improve detection capability of the probe 400 over predecessor probes. For example, with 3 gas permeable membranes instead of 1, can yield triple the mass transfer into the probe. O-ring port 420 can accommodate an O-ring such as, e.g., MS16142 O-Ring available from PARKER HANNIFIN CORPORATION, O-Ring Division, of Lexington, Ky., U.S.A. The inner core barrel assembly 404 as shown in FIG. 4C is made to receive the heater element 406, allowing for expansion. FIG. 4C depicts diagram 450, in an exemplary embodiment, including a side view (at bottom), and two cross-sections A-A (middle), and B-B (top), respectively, illustrating the inner core barrel assembly 404 having O-Ring grooves for gas passages, where the O-rings serve to seal the gas passages.

4. In an exemplary embodiment, the enhanced MIP 400 can include an incorporated watertight integrity through a major redesign of the probe body and mechanical couplings 424 and electrical couplings 410, 411, 416 because water intrusion has been identified as a major contributor to premature probe failure.

5. In an exemplary embodiment, the enhanced MIP 400 can include a simpler design to allow for field repairs and replacement of individual components (e.g., the heater system 416). Currently, failure of any component of conventional probes require complete replacement of the probe increasing the cost of operation and delay. As noted above, the various modules and subsystems of enhanced probe 400 allow field replacement of failing components.

6. In an exemplary embodiment, the enhanced MIP 400 can include integrating small removable traps directly into the probe for the collection and concentration of volatile organic compounds. The removable trap feature can allow for lower (better) detection levels of compounds as well as the specific identification of compounds through post run chromatographic analysis.

7. In an exemplary embodiment, the enhanced MIP 400 can include incorporating a heated transfer line from the probe body to the surface detector suite to minimize the current loss of volatile organic compounds in the cold transfer line. As shown, the probe can have a custom heater element 406 with a through conductor and ground conductor. A heater cartridge insert 406 can be provided.

8. In another exemplary embodiment, the enhanced MIP 400 can include a detector suite, and sample introduction system specifically configured for the MIP application. This feature can reduce the overall equipment footprint and cost; allow for the introduction of calibration/tracer gases; and allow for the simultaneous sampling of the volatile organic gas stream for immediate chromatographic analysis. See FIG. 9A and 9B below and the discussion with reference to these figures of the enhanced scanning solutions module.

9. In an exemplary embodiment, the enhanced MIP 400 can include an integrated global positioning system (GPS) receiver along with the data acquisition system to allow for simultaneous positioning of sampling points with the sample data for the volatile organic compounds. A smart integrated GPS probe can allow easier closely integrated geo-referencing of captured sample data.

10. In yet another exemplary embodiment, the enhanced MIP 400 can include integrating a wireless data transfer communication device with the data acquisition system to allow for near real time transfer of data to a base station for subsequent analysis and display. In an exemplary embodiment, the wireless data transfer communication device can include transceiver hardware for wireless transmission. A communications protocol software application suite stack can accompany the transceiver hardware feature to provide various functions. In an exemplary embodiment, the wireless communications device can be compliant with an IEEE standard 802.11 wireless local area network. In another exemplary embodiment, other wireless hardware and software protocols can be used such as, e.g., ultrawideband (UWB), cellular, global system for mobile telephone (GSM), code division multiple access (CDMA), orthogonal frequency division multiple access (FDMA), cellular digital packet data (CDPD), or other wireless protocols and technologies.

11. In an exemplary embodiment, the enhanced MIP 400 can include providing for a mobile computing/communications device that can be in an exemplary embodiment, handheld, and can include a graphical display and control module for system operation and data acquisition. The mobile computing/communications device feature enhances the operator's mobility during field sampling events. In one exemplary embodiment, the mobile device can be a portable device such as, e.g., the self-contained portable sensor system illustrated in FIG. 11.

12. In an exemplary embodiment, the enhanced MIP 400 can include providing for the simultaneous trapping and concentration of volatile organic compounds during MIP sampling and logging events. The simultaneous trapping and concentration of volatile compounds can allow for near real-time specific identification of the volatile organic compounds detected.

13. In an exemplary embodiment, the enhanced MIP 400 can include providing for calibration of the probe system using chromatographic methods such as internal standards.

D. Project Management
Capabilities:
Web Interface
User-based access levels
Maintain multiple projects
Maintain Project History
Create new projects
Upload files
Communicate with field computer in real-time The solution to the challenges mentioned above is an intelligent project maintenance, data acquisition and analysis process. The process of the present invention can be done by combining a variety of technologies and procedures in a novel manner. A complete solution spans from project maintenance to final result presentation. No such solution conventionally exists prior to the present invention.

Project maintenance is available through a Web interface. This interface allows the project manager to create new jobs and to upload project information for distribution to field computers using technologies such as, e.g., wireless communications links. The web interface can also serve as a centralized project plan ("project central") for the project managers. At the web interface, the project managers can follow the progress of a job on an up-to-the-minute basis, allowing the project managers to make critical changes and adjustments to the project plan in a real-time environment. Changes made to the project plan can be immediately propagated into the field via communications links to mobile devices such as wireless field computers. Project managers can maintain an infinite number of projects simultaneously through the web interface.

A main feature of the web interface can include a status "dashboard" which can display to the project manager exactly how the project is proceeding at a glance. The system can also include email notifications triggered by project changes where the email notifications can be put into effect, alerting the project manager of changes. Field personnel can also communicate problems and request replacement parts through the web interface, making the web interface the complete solution for remote project maintenance.

E. Sensor and its Connection to the Field Computer
Capabilities:
Web Interface

To fill the need for more complete information at the point of sampling, project information can be accessible in the field on a mobile device, such as, e.g., a wireless handheld computer. Information such as site maps can be available to the operator of the mobile device at the touch of a button. This information can also be remotely updated by the project manager using the web interface. The field operator can also make ad hoc changes to the project on-the-fly as needed. These changes will be transmitted back to the project management site where an alert can be issued to the project manager. The ability to make field decisions without loosing project plan cohesiveness is a vital component of a complete solution.

During the data collections process, the operator can be guided by the field computer that serves as an expert system, conveying "best practices" to any operator regardless of experience. The operator can have full access to all site information including the locations of the proposed sampling points.

The advanced sensor equipment can interface to the field computer during the collections process, providing visual feedback and data storage/retrieval.

F. Link to Global Positioning Satellite (GPS) Receiver

Capabilities:

Sub-meter accuracy

Altitude

Communications through standard personal computer (PC) communications ports (COM (RS-232 serial), LPT (parallel), USB(universal serial bus))

Streaming location data

During the data collections phase, the field computer can also be linked to a global positioning system (GPS) antenna. The GPS can allow the field operator to accurately locate any predefined locations that are part of the pre-loaded site plan. Of course alternative location positioning systems can be used using conventional approaches such as, e.g., triangulation, and satellite transmitter location systems. The GPS can also provide the ability to adjust locations due to unexpected obstacles without loosing location accuracy in the final output. The GPS capability can also negate the need for the site to be surveyed by a 3rd party, as is conventionally the norm absent the present invention, thus providing time and cost reductions to the overall process. The GPS data can be transmitted along with all collected data as a complete package. The packaged information can then be incorporated in the "dashboard" on the web interface to show progress.

By providing altitude information along with geographic two-dimensional (2D) coordinates, typography can be added to the three-dimensional (3D) images, resulting in a more "realistic" picture of the site and its below-ground behavior. An exemplary 3D visualization rendering is provided from an exemplary embodiment of the present invention in FIG. 3 of the present invention.

G. Data Transmission Process

Capabilities:

Hypertext transfer protocol (HTTP) POST

HTTP GET

Transmission control protocol/Internet Protocol (TCP/IP)

Simple mail transfer protocol (SMTP)

File transfer protocol (FTP)

Data can be transmitted via a communications network 1004 as shown in FIG. 10A. The data can be transmitted over a wireless communications link where available. If wireless access is not available, the system can equally connect to the main system via any conventional method including, e.g., a dialup connection, or other direct network connection with accompanying protocol communications software applications suite. Due to the various wireless communications technologies available, a one-size-fits-all approach is not desirable. The solution in an exemplary embodiment of the present invention, includes a comprehensive open software international (OSI) layer 4, transport layer TCP built on a standards-based protocol suite to utilize the inherent capabilities of whatever wireless device and network is being used. The OSI layer 2, link layer, such as Ethernet, or other media access control (MAC) protocols can therefore be largely ignored and thus can make the approach of the present invention largely immune to changing technologies. The transport protocol layer is based on standard Internet protocols, the transmission control program (TCP). Since push capabilities do not exist on all data networks, polling by the field computer can be employed as a means to acquire updated information from the main system.

H. Database

Capabilities:

Relational Database

Support for standard structured query language (SQL) query tools

Support for open database connectivity (ODBC) compliant databases

Scalability

Once new data has been transmitted to the main system, the data can be stored in the database under its parent project. All data can be organized in a parent/child relationship. (Customer->Project->Data)

I. Analysis

Capabilities:

Modular

Remove Baseline Drifts

Normalize data between samples

Output to Database

Multi-pass analysis for "smoothing" of results

Pattern recognition

Cross Analysis with external data

Site, Geology, and Chemistry Comparisons

Risk Evaluation and Assessment

Analysis of the data can occur when sufficient amounts of data have been collected. This process can be governed by a user-defined setting in the project and can be stored in the database. The field operator can also request seatrain types of analysis to be made on-the-fly, to guide the decision making process. Depending on the type of data collected, a number of data "normalization" processes can be executed. The normalization processes can be designed to correct data for such anomalies such as, e.g., "drifting baseline," "change in temperature," "peak to baseline height," "conductivity," and "atmospheric pressure." The normalization processes can produce more accurate results and can be a vital step in the process. Not normalizing results can lead to a varying degree of confidence and thus can create an environment where the findings could be misleading.

The normalization process can use historical data for reference and can thus become more accurate with a larger number of samples.

3D analyses can include volumetric probability calculations like "kriging" and surface area contour mapping. All analyzed data can be stored in the database under the parent project and can be added to the "dashboard" for comparative analysis by the project manager. Once analysis of the data has been completed the project manager can have a new set of tools available through the web interface. Using these tools such questions as "How much overburden must be removed to reach the source area?" can be answered.

The analysis process takes into account all relevant information provided in the project. To gain further refinement of the results, the project manager can upload such information as ground water tables and geological data. The project manager can "force" new analysis at any time to include newly uploaded information.

J. 3-Dimensional Visualization, Display

Capabilities:

Display volumetric data in form of "plumes"

Transparency of objects

Overlay computer aided design (CAD) drawings and other geographic information system (GIS) file formats Calculate volume and mass Drill-down information popup Convex hull grid North directional arrow Overview window (birds-eye view)

Custom selectable colors

Coloring based on confidence

Object-based editing

Image output in, e.g., BMP, JPG, TIF extension image formats

The project manager can select a number of "pre-defined" 3D visualizations, graphics, outputs through the web interface. These standard "views" can be produced automatically by the 3D modeling software once the analysis process is complete. The views can then be made available to the project manager through the web interface. Another option available to the project manager can be to have an expert produce custom "views" from the data collected. The expert can use a specially designed graphical user interface (GUI) to produce 3D objects from the data produced by the analysis process. The GUI can provide an easy and fast environment in which the expert can drag and drop visual elements onto the "presentation screen" to accomplish tasks. Each object can have a number of behaviors or properties. After being added to the presentation screen the expert can manipulate the output through these capabilities.

The interface can allow the expert to create "screen shots" of the presentation screen at any time. These screen shots can be saved as both images (e.g., bitmaps) and "presentation objects" which can be manipulated in 3D. These 3D objects can be rotated and zoomed using a viewer, but can only be altered by the expert. This can provide a very powerful way to distribute 3D images as it allows the end user to fine tune the view and to insure visibility of vital information.

The 3D modeling system can also produce high quality movies in all major formats (e.g., MPEG, AVI, MOV, etc.). Output can be provided electronically over the web, or on a compact disk-read only memory (CD-ROM) or digital versatile disk (DVD) depending on user preference.

K. Interactive Presentation
Capabilities:
Server/client communication over TCP/IP
Real-time remote manipulation
Save data on both server and client
Permission based Client manipulation
Read Database through ODBC
ActiveX
Support 56 kps connection speed
Object inventory based on available data
Multiple clients connecting to one server
Multiple client screen resolutions shown on server
Client Connection dashboard on server A vital part of the 3D modeling process is the interaction by the end user. Through a live interface between the end user's "client software" and the expert's "server software," the end user can play an active role in the creation of the final product. The link between the two systems can run over a TCP/IP connection. The end user can see the same screen output as viewed by the expert and can have the ability to manipulate the objects on the screen to insure a collaborative result. The expert can be responsible for the introduction of new screen elements such as grid line and contamination plumes. Each resulting "screen shot" can be saved in the customer's inbox and can be immediately available on the end user's system as well. This data can now be available for view and re-distribution at any time by the end user. Information about the produced screen shots can be saved in the database and can become the basis for billing.

L. Mobile Device—Handheld Mobile Computer

The mobile device, also referred to as a field computer, serves a number of purposes. First and foremost it is the link between the collected data and the main system, but it is also a tool to be used by the field operator. It includes guides and "best practices" approaches to field operations. Through the 3D feedback mechanism, the operator will have visibility of the results from the analysis and 3D modeling right in the field. The analysis data will be returned timely enough to be used in the selection of the next sample location, thus giving the operator the advantage of only addressing locations that are deemed vital to the results.

Analyses returned to the field computer include "next location" suggestions along with calibration information produced by the normalization process. The ability to make field decisions in real-time is a great time and cost saver. Examples of the field computer can include any mobile device such as, e.g., a desktop, notebook, laptop, subnotebook, tablet or handheld personal computers (PCs), or personal digital assistants (PDAs). The field computer 500a in an exemplary embodiment, can be in wireless communication with a base station computer 500b (collectively computers 500). In an exemplary embodiment, the mobile device 500a can communicate with the base station computer device 500b using any of a number of well known wireless communications software protocols, transceiver hardware, networks and communications link technologies such as, e.g., an Infrared Data Association (IrDA)-compliant wireless technology, or a short range radio frequency (RF) technology such as, e.g., a Bluetooth-compliant wireless technology, an IEEE standard 802.11-compliant wireless local area network (LAN) such as, e.g., an IEEE standard 802.11a, b, or g, wireless LAN, a Shared Wireless Access Protocol (SWAP)-compliant wireless technology, a wireless fidelity (Wi-Fi)-compliant wireless technology, or an ultra wide band (UWB) wireless technology network. Although mobile device 500a and base station computer device 500b have been described as coupled to one another, the devices 500a,b need not be directly connected to one another, and can instead by coupled by any of various conventional physical network technologies such as, e.g., routers, bridges, gateways, transceivers, antennae and cables.

III. Example Implementations

Figure 5:
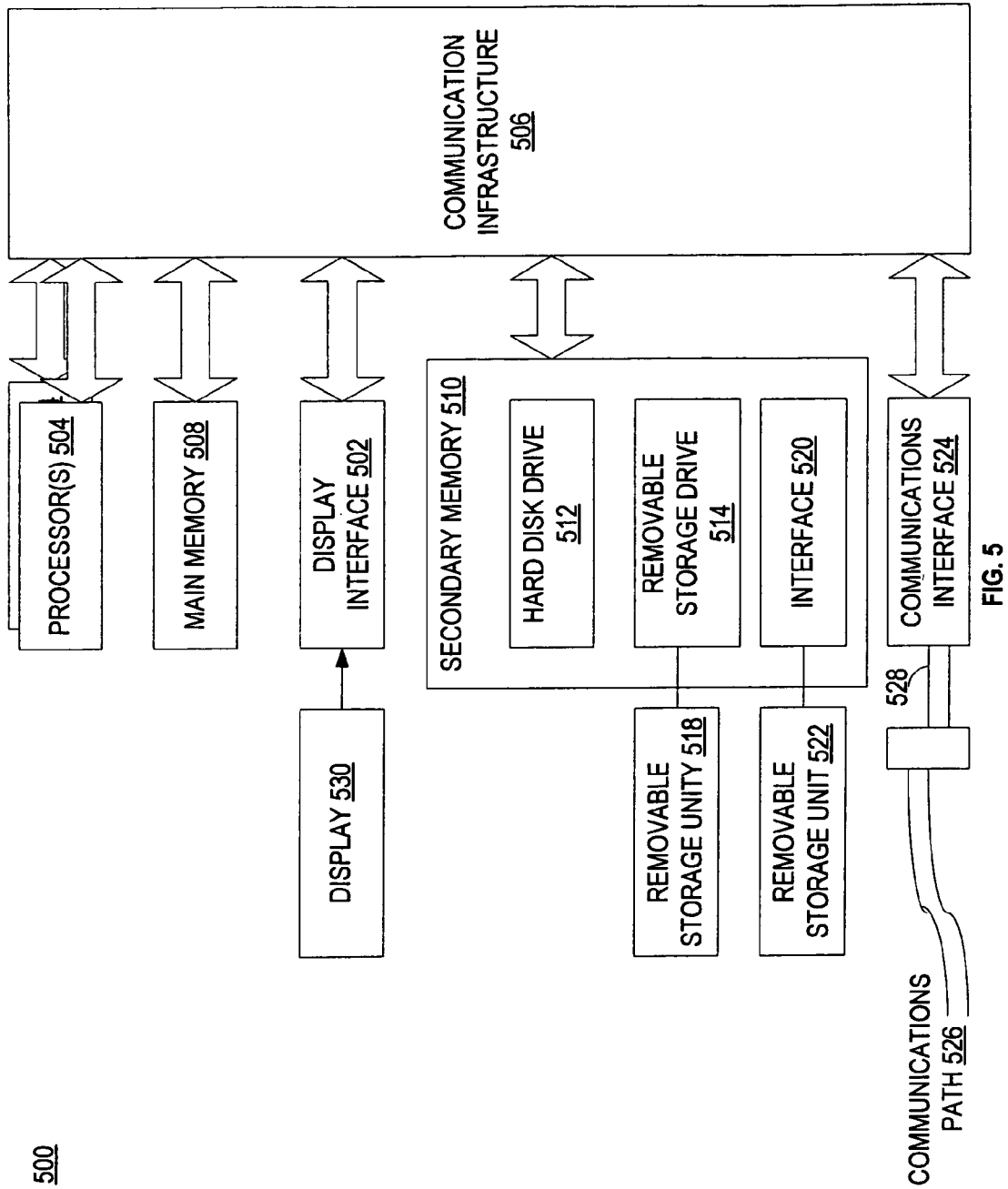
FIG. 5 depicts an exemplary embodiment of a block diagram of an exemplary computer system useful for implementing the present invention.

The present invention (or any part(s) or function(s) thereof) may be implemented using hardware, software or a combination thereof and may be implemented in one or more computer systems or other processing systems. In fact, in one exemplary embodiment, the invention is directed toward one or more computer systems capable of carrying out the functionality described herein. An example of a computer system 500 is shown in FIG. 5. FIG. 5 depicts an exemplary embodiment of a block diagram of an exemplary computer system useful for implementing the present invention. Specifically, FIG. 5 illustrates an example computer 500 in a preferred embodiment is a personal computer (PC) system running an operating system such as, e.g., Windows 98/2000/XP, Linux, Solaris, OS/2, Mac/OS, or UNIX. However, the invention is not limited to these platforms. Instead, the invention can be implemented on any appropriate computer system running any appropriate operating system, such as Solaris, Irix, Linux, HPUX, OSF, Windows 98, Windows NT, OS/2, Mac/OS, and any others that can support Internet access. In one exemplary embodiment, the present invention is implemented on a computer system operating as discussed herein. An exemplary computer system, computer 500 is shown in FIG. 5. The mobile device 500a can be a communications device or computing device such as, e.g., a tablet personal computer (PC), a handheld PC, a handheld running WINDOWS MOBILE for POCKET PC operating system, a subnotebook PC a notebook PC, a laptop PC, a personal digital assistant (PDA), or other device such as a desktop PC or workstation. Although mobile device 500 in an exemplary embodiment is described as mobile, the device need not be mobile, and can actually be stationary. The base device 500b can be another mobile device, a desktop computer, or some other source of data that can be synchronized with the data on the mobile device 500a.

Other components of the invention, such as, e.g., a computing device, a communications device, a telephone, a personal digital assistant (PDA), a pocket personal computer (PC), a handheld personal computer (PC), client workstations, thin clients, thick clients, proxy servers, network communication servers, remote access devices, client computers, server computers, routers, web servers, data, media, audio, video, telephony or streaming technology servers could also be implemented using a computer such as that shown in FIG. 5.

The computer system 500 includes one or more processors, such as processor 504. The processor 504 is connected to a communication infrastructure 506 (e.g., a communications bus, cross-over bar, or network) Various software embodiments are described in terms of this exemplary computer system. After reading this description, it will become apparent to a person skilled in the relevant art(s) how to implement the invention using other computer systems and/or architectures.

Computer system 500 can include a display interface 502 that forwards graphics, text, and other data from the communication infrastructure 506 (or from a frame buffer not shown) for display on the display unit 530.

The computer system 500 also includes a main memory 508, preferably random access memory (RAM), and a secondary memory 510. The secondary memory 510 can include, for example, a hard disk drive 512 and/or a removable storage drive 514, representing a floppy diskette drive, a magnetic tape drive, an optical disk drive, a compact disk drive CD-ROM, etc. The removable storage drive 514 reads from and/or writes to a removable storage unit 518 in a well known manner. Removable storage unit 518, also called a program storage device or a computer program product, represents a floppy disk, magnetic tape, optical disk, compact disk, etc. which is read by and written to by removable storage drive 514. As will be appreciated, the removable storage unit 518 includes a computer usable storage medium having stored therein computer software and/or data.

In alternative exemplary embodiments, secondary memory 510 may include other similar devices for allowing computer programs or other instructions to be loaded into computer system 500. Such devices may include, for example, a removable storage unit 522 and an interface 520. Examples of such may include a program cartridge and cartridge interface (such as, e.g., those found in video game devices), a removable memory chip (such as, e.g., an erasable programmable read only memory (EPROM), or programmable read only memory (PROM) and associated socket, and other removable storage units 522 and interfaces 520, which allow software and data to be transferred from the removable storage unit 522 to computer system 500.

Computer 500 can also include an input device such as (but not limited to) a mouse or other pointing device such as a digitizer, and a keyboard or other data entry device (none of which are labeled).

Computer 500 can also include output devices, such as, for example, display 530, and display interface 502. Computer 500 can include input/output (I/O) devices such as, e.g., communications interface 524, cable 528 and communications path 526. These can include, e.g., a network interface card, and modems (neither are labeled). Communications interface 524 allows software and data to be transferred between computer system 500 and external devices. Examples of communications interface 524 may include a modem, a network interface (such as, e.g., an Ethernet card), a communications port, a Personal Computer Memory Card International Association (PCMCIA) or PCCard-compliant slot and card, etc. Software and data transferred via communications interface 524 are in the form of signals 528 which may be electronic, electromagnetic, optical or other signals capable of being received by communications interface 524. These signals 528 are provided to communications interface 524 via a communications path (e.g.,channel) 526. This channel 526 carries signals 528 and may be implemented using wire or cable, fiber optics, a telephone line, a cellular link, an radio frequency (RF) link and other communications channels.

In this document, the terms "computer program medium" and "computer usable medium" are used to generally refer to media such as, e.g., removable storage drive 514, a hard disk installed in hard disk drive 512, and signals 528. These computer program products provide software to computer system 500. The invention is directed to such computer program products.

Computer programs (also called computer control logic), including object oriented computer programs, are stored in main memory 508 and/or the secondary memory 510 and/or removable storage units 514, also called computer program products. Such computer programs, when executed, enable the computer system 500 to perform the features of the present invention as discussed herein. In particular, the computer programs, when executed, enable the processor 504 to perform the features of the present invention. Accordingly, such computer programs represent controllers of the computer system 500.

In another exemplary embodiment, the invention is directed to a computer program product comprising a computer readable medium having control logic (computer software) stored therein. The control logic, when executed by the processor 504, causes the processor 504 to perform the functions of the invention as described herein. In another exemplary embodiment where the invention is implemented using software, the software may be stored in a computer program product and loaded into computer system 500 using removable storage drive 514, hard drive 512 or communications interface 524. The control logic (software), when executed by the processor 504, causes the processor 504 to perform the functions of the invention as described herein.

In yet another embodiment, the invention is implemented primarily in hardware using, for example, hardware components such as application specific integrated circuits (ASICs), or one or more state machines. Implementation of the hardware state machine so as to perform the functions described herein will be apparent to persons skilled in the relevant art(s).

In yet another exemplary embodiment, the invention is implemented using a combination of both hardware and software.

Figure 6:
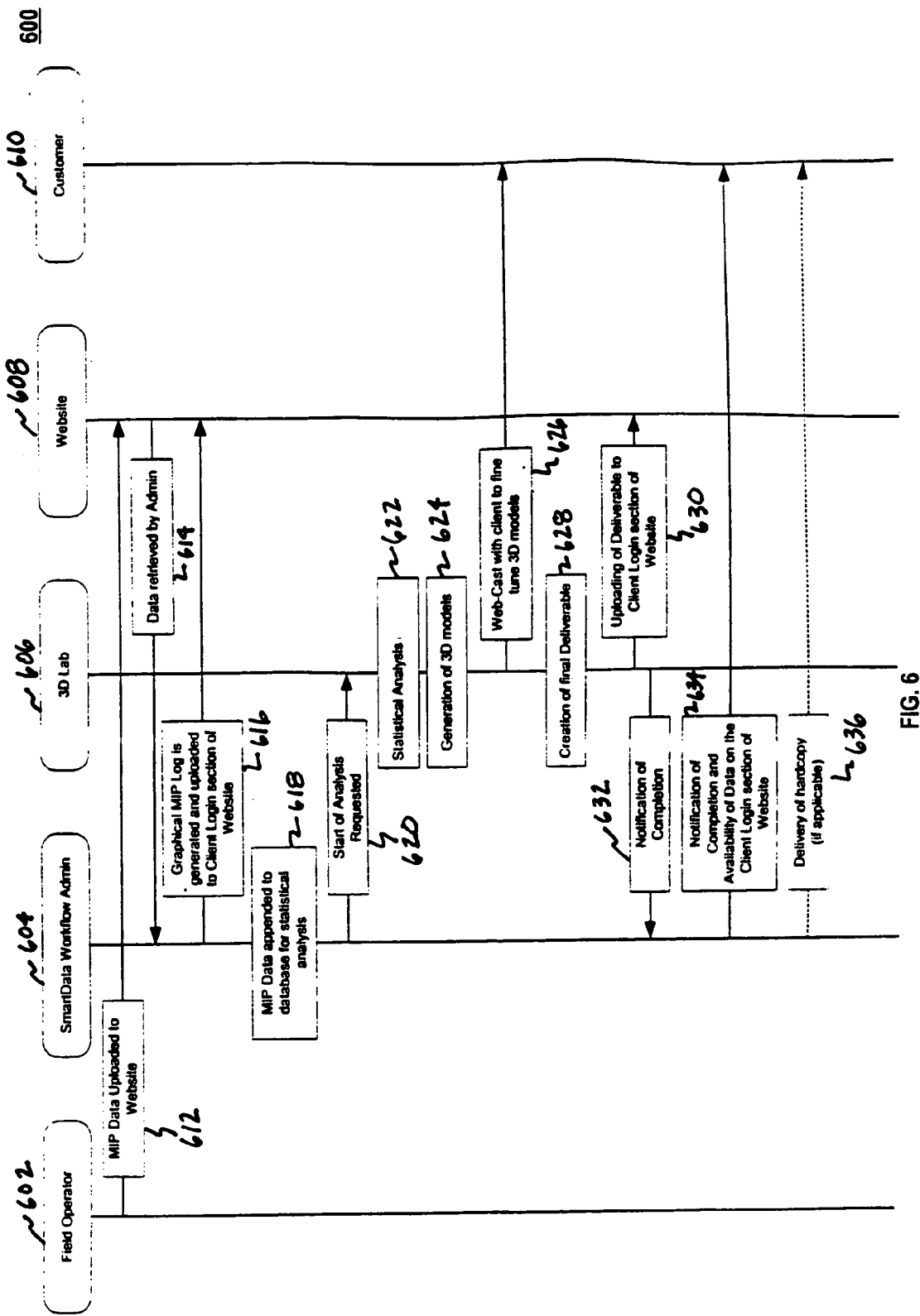
FIG. 6 depicts an exemplary embodiment of a workflow process according to an exemplary embodiment of the present invention.

FIG. 6 depicts an exemplary embodiment of diagram 600 illustrating an exemplary workflow process according to an exemplary embodiment of the present invention. The workflow process of diagram 600 includes workflow between a field operator 602, a SmartData Workflow Administrator 604, a 3D Lab 606, a Website 608, and a customer user 610. The workflow process of diagram 600 begins with a field operator 602 from which MIP data is uploaded to website 608 as shown in step 612. From Website 608, data is retrieved by SmartData Workflow Administrator 604 as shown in step 614. From SmartData Workflow Administrator 604, a graphical MIP log is generated and uploaded to client login section of the website 608 as shown in step 616. Meanwhile MIP data is appended to the database for statistical analysis in step 618 and as shown in step 620, a start of analysis is requested of the 3D Lab 606. 3D Lab 606 performs statistical analysis in step 622. Various kinds of statistical analyses can be performed as will be apparent to those skilled in the relevant art(s). Processing can include, e.g., calculating means, standard deviations, Kriging, correlation analysis, interpolations, extrapolations, etc. Then 3D lab 606 can generate 3D models as shown in step 624. Then 3D Lab 606 can web-cast with the client customer user 610 to fine tune 3D models as shown in step 626. Then a final deliverable can be created as shown in step 628 by 3D Lab 606. Then the 3D Lab 606 can upload the deliverable to the client login section of the website 608 as shown in step 630. Then the 3D Lab 606 can provide a notification of completion to SmartData Workflow Administrator 604 as shown in step 632. Then the SmartData Workflow Administrator 604 can provide notification to customer user 610 of completion and availability of data on the client login section of the website as shown in step 634. Finally, SmartData Workflow Administrator 604 can provide delivery of a hardcopy (if applicable) to customer user 610 as shown in step 636.

Figure 7:
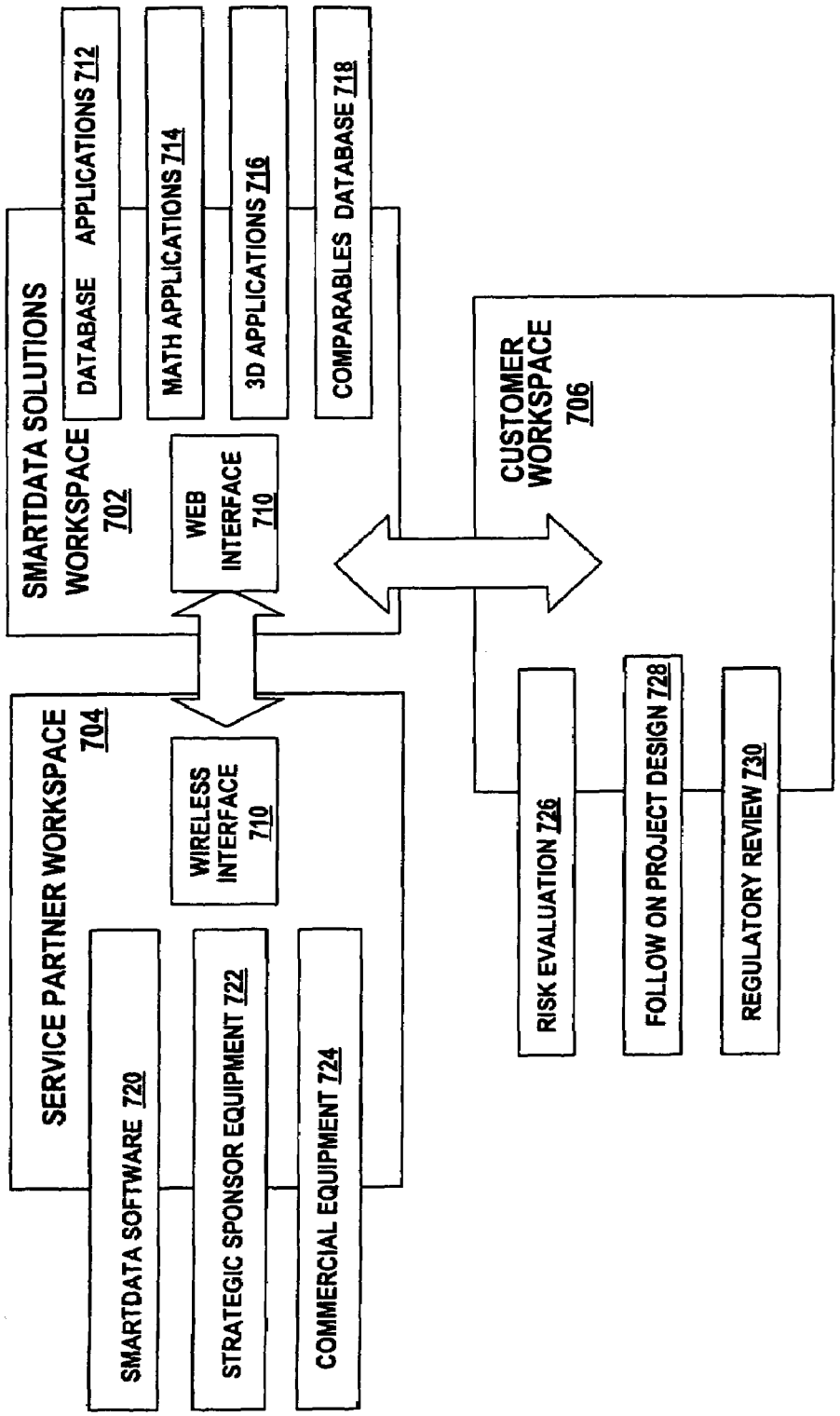
FIG. 7 depicts an exemplary embodiment of an overall smart data system process according to the present invention.

FIG. 7 depicts an exemplary embodiment of a diagram 700 illustrating an overall smart data solutions architecture system process according to the present invention. Smartdata solutions workspace 702 includes database applications 712, math applications 714, 3D applications 716, and comparables database 718. The Smartdata solutions workspace 702 also includes a web interface 710 for communication of information to service partner workspace 704, via wireless interface 710. The service partner workspace 704 includes smartdata software 720, strategic sponsor equipment 722, and commercial equipment 724. The Customer workspace 706 can also interact with Smartdata solutions workspace 702 as represented by the bidirectional arrows indicated in diagram 700. Customer workspace 706 includes risk evaluation 726, follow-on project design 728, and regulatory review 730.

FIG. 8A depicts an exemplary embodiment of a diagram 800 of an exemplary, conventional MIP data acquisition system according to the present invention. The exemplary MIP system of diagram 800 includes a MIP probe 810 (e.g., the MIP disclosed in the '956 patent), a MIP controller 802, a detector system 804 and a data acquisition module 806 coupled to both the MIP controller 802 and detector system 804. The MIP probe 810 is coupled to MIP controller 802 and detector system 804, by a trunk line and connections 808. The data acquisition module 806 takes its inputs and outputs data typically in the form of a data stream.

Figure 8B:
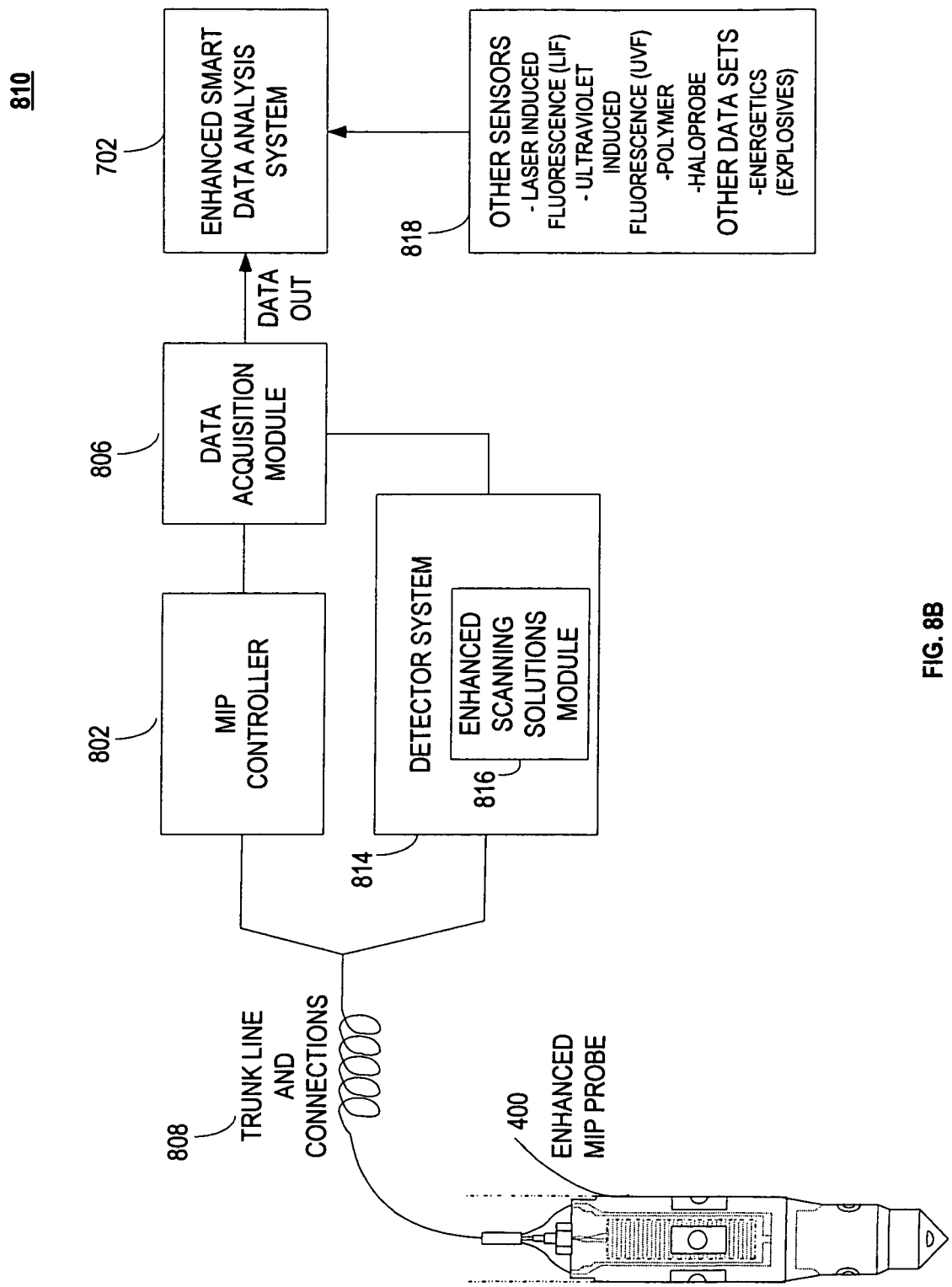
FIG. 8B depicts an exemplary embodiment of an improved MIP system including an enhanced MIP probe, a controller, an enhanced scanning solutions module detector system, data acquisition module, and an enhanced smart data system according to the present invention.

FIG. 8B depicts an exemplary embodiment of a diagram 810 of an improved MIP environmental data acquisition and analysis system according to an exemplary embodiment of the present invention. The improved MIP system of diagram 810 includes an enhanced MIP probe 400 coupled to MIP controller 802 and detector system 814, by a trunk line and connections 808. The detector system 814 is enhanced to include an enhanced scanning solutions module detector system 816 described further below with reference to FIGS. 9A and 9B. The detector system 814 and MIP controller 802 are again coupled to data acquisition module 806. The output of the data acquisition module 806 is coupled to an enhanced smart data analysis system 702 as shown in diagram 810. The enhanced smart data analysis system 702 can receive other input sensors 818, which may, or may not be from sensors integrated into the MIP probe 812. Examples of other sensors 818 include, e.g., laser induced fluorescence (LIF), ultraviolet induced fluorescence (UVF), polymer, and haloprobe. The enhanced smart data analysis system 702 can also receive other input data sets such as, e.g., energetics (explosives) data, computer aided design (CAD) drawing data, ground water (GW) data (see FIG. 12B) and geographic information systems (GIS) data.

Figure 9A:
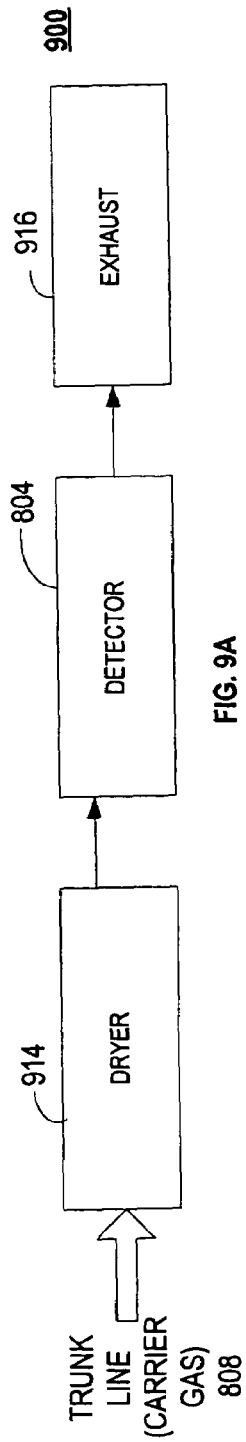
FIG. 9A depicts a diagram illustrating an exemplary embodiment of a conventional detection system according to the present invention.

FIG. 9A depicts an exemplary embodiment of a diagram 900, illustrating functionality of a conventional detection system. The detection system of diagram 900 begins with a trunk line 808 coupling a MIP (not shown) to a dryer 914. The dryer 914 is conventionally coupled to the detector 804. The detector is in turn coupled to an exhaust 916. Unfortunately, the conventional system is limited, inflexible and sequential in its processing as compared to the present invention as depicted in and described further below with reference to FIGS. 9B and 9C.

Figure 9B:
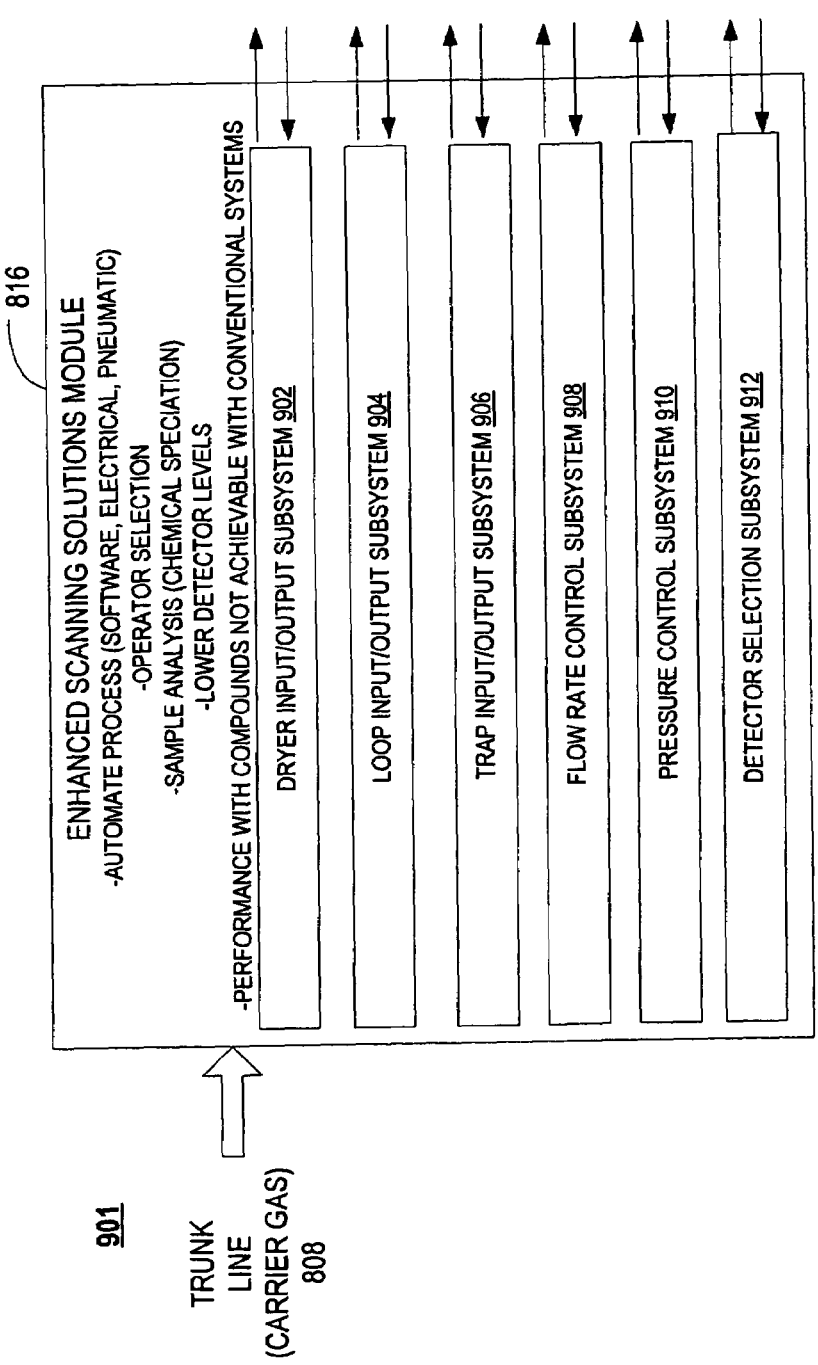
FIG. 9B depicts a high level diagram illustrating an exemplary embodiment of an enhanced scanning solutions module according to the present invention.

FIG. 9B depicts an exemplary embodiment of a high level diagram 901 illustrating an enhanced scanning solutions module 816 according to the present invention. The enhanced scanning solutions module 816 provides such features as, e.g., automating the detector process including software control, electronics, flow control, and pneumatic systems. The enhanced scanning solutions module 816, in an exemplary embodiment, can provide for operator selection, sample analysis leading to chemical speciation, lower detector levels, and performance with compounds not conventionally achievable. The enhanced scanning solutions module 816, in an exemplary embodiment, can receive as input the trunk line 808 with carrier gas from the MIP 400 as shown in FIG. 8B. The enhanced scanning solutions module 816, in an exemplary embodiment, can include several subsystems including one or more of, e.g., a dryer input/output subsystem 902; a loop input/output subsystem 904; a trap input/output subsystem 906; a flow rate control subsystem 908; a pressure control subsystem 910; and a detector selection subsystem 912.

Figure 9C:
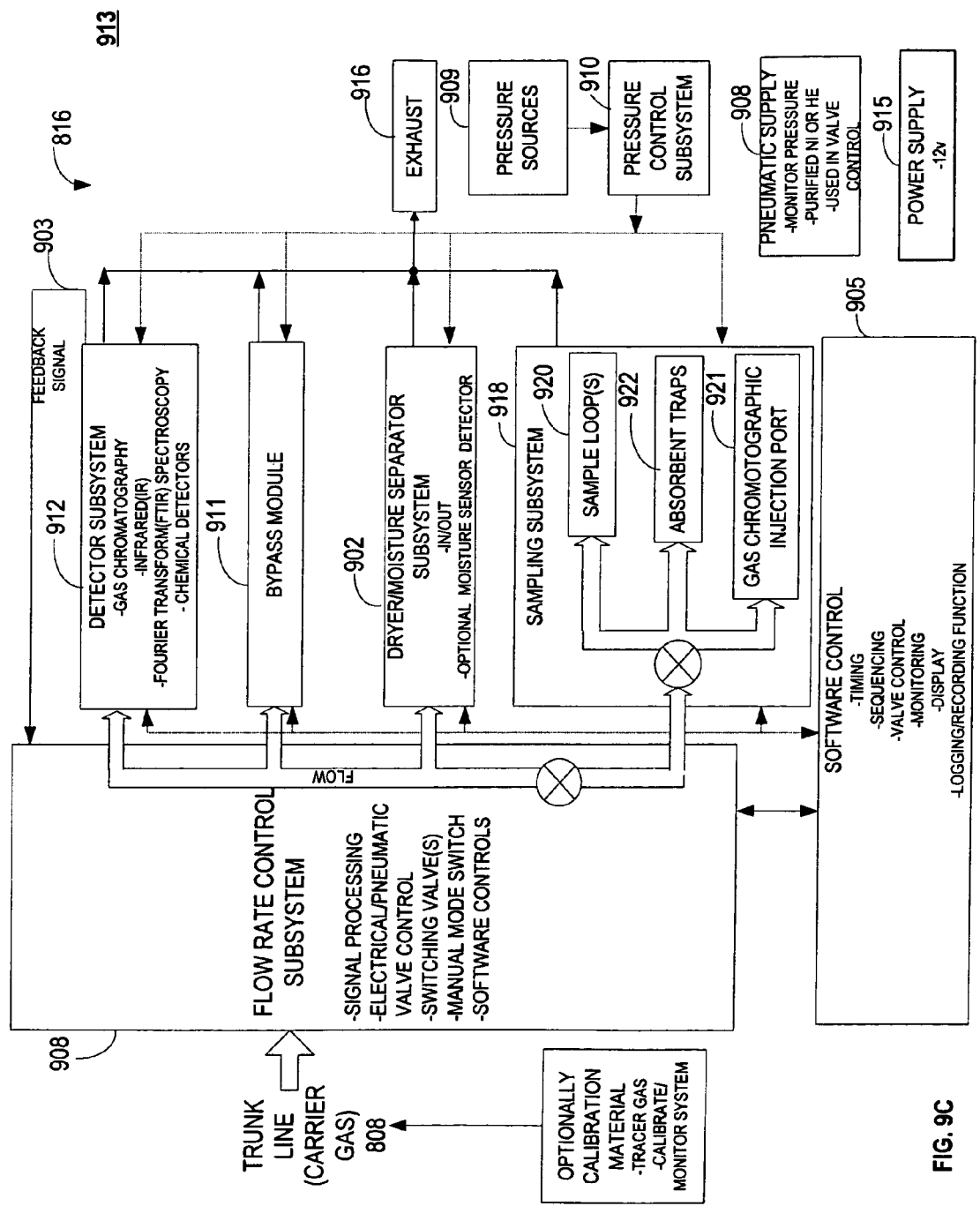
FIG. 9C depicts a more detailed version of an exemplary embodiment of exemplary enhanced scanning solutions functionality according to the present invention.

FIG. 9C depicts an exemplary embodiment of a detailed level diagram 913 illustrating an enhanced scanning solutions module 816 according to the present invention. The enhanced scanning solutions module 816 can receive from the MIP 400, a carrier gas on trunk line 808, at the flow rate control system 908. The flow rate control system 908 can include such functionality as one or more of, e.g., signal processing, electrcical/pneumatic valve control, switching valves, manual mode switch, and software controls. The flow rate control system 908 can allow custom workflow by selecting in or out particular detection subsystems. Exemplary subsystems can include, e.g., detector subsystem 912, a bypass module 911, dryer/moisture separator subsystem 902, sampling subsystem 918, pressure control subsystem 910 and pressure sources 909, pneumatic supply subsystem 908, exhaust 916, software control subsystem 905, and power supply 915.

The sampling subsystem 918 in an exemplary embodiment can include any of, e.g., sample loop(s) 920, absorbent traps 922, and gas chromatographic injection ports 921. In an exemplary embodiment, the sampling subsystem can be software controlled.

To calibrate the system, in an exemplary embodiment, an optional calibration material such as, e.g., a tracer gas can be run through the system and results can be measured and analyzed, and used for calibration, and for normalization procedures.

The detector subsystem 912, in an exemplary embodiment, can include any of various detectors, such as, e.g., gas chromatography, infrared (IR), Fourier transform infrared (FTIR) spectroscopy, and chemical detectors. The detector subsystem can be coupled to exhaust 916, pressure control subsystem 910, software control system 905, as well as the flow control system 908. From the output of detector 812, an input is provided to exhaust 916. From sampling module 918, an output is provided as input to sample loop 920 and concentration trap 922.

The bypass module 911 can, e.g., bypass detection.

The dryer/moisture separator subsystem 902 can be used to bring in or out the dryer and by being software controllable, can be incorporated into processing on an ad hoc basis, as selected by the user.

The pressure control subsystem 910 and pressure sources 909 can provide back pressure to the system. Pressure can be added to any of the processes including, e.g., the detector subsystem 912, a bypass module 911, dryer/moisture separator subsystem 902, and sampling subsystem 918.

The pneumatic supply subsystem 908 can include, e.g., purified He or Ni, and can be used in valve control. The pneumatic supply subsystem 908 can be software controlled. The software control system 905 can monitor pressure, and can control outlet options.

The software control subsystem 905 can provide various functions including any of, e.g., timing, sequencing, valve control, monitoring, displaying data, logging data and recording data.

The power supply 915 can provide power to electrical components. In an exemplary embodiment, a 12 V DC battery supply can be used.

Using the enhanced scanning solutions module 816, a user can specify a user-directed detection process. For example, output of a concentration trap can be sent to detectors, or a detector on a second system such as, e.g., a chemical analysis detector. As another example, using the present invention, use of a dryer can be optional. Thus, as these examples illustrate, a user can on a ad hoc basis direct a customized detection process, that allows for interactive changes to the detection process.

FIG. 10A depicts an exemplary embodiment of an exemplary diagram 100 illustrating a hardware system architecture according to the present invention. Diagram 100 includes a user 206a at a mobile device 1002a in communication over network 1004 to the enhanced smart data analysis system application servers 1010a, 1010b to access data on database 1008, via web servers 1006a, 1006b providing an exemplary enhanced smart data analysis client-server system. If licensed, then user 206a can gain access via software link 208 and browser link 210. Other users archiver 206b, viewer 206c and collector 202.

FIG. 10B depicts an exemplary embodiment of an enhanced smart data analysis system 702 according to the present invention. The enhanced data analysis system 702 includes an application service provider (ASP) 1010 by which a variety of users 206a can share the use of application servers 1010a, 1010b of the ASP for a fee. An exemplary embodiment of the enhanced data analysis system 702 can include various subsystem modules including, e.g., a database management system 1008 and storage/retrieval/search query subsystem 1012; processing subsystem 1014, algorithms module 1016, formatting module 1018, 3D/2D visualization 1020; and communications protocols 1022, web delivery 1024, webcast 1026, field wireless delivery 1028, and wireless receiver 1030.

Figure 11:
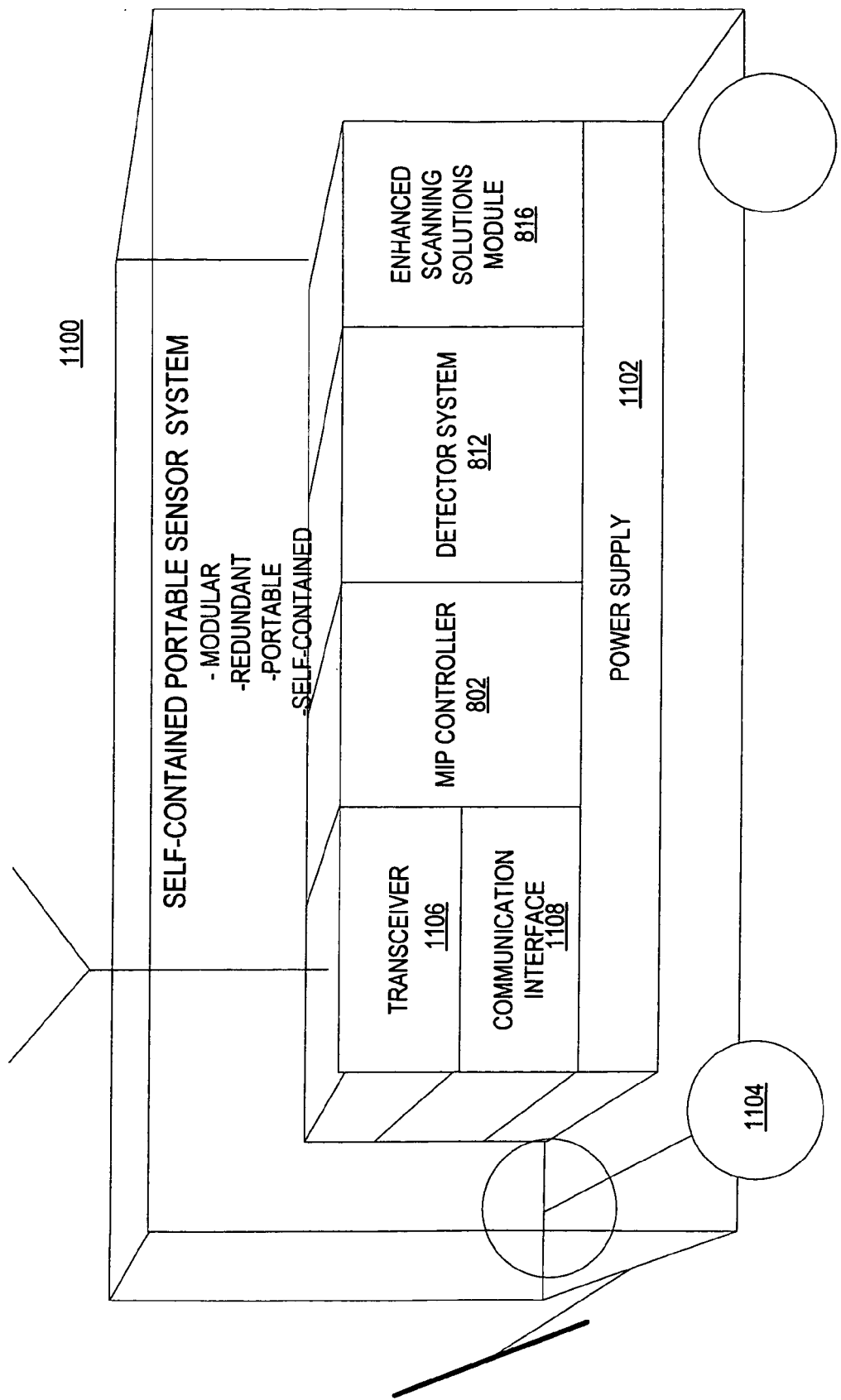
FIG. 11 depicts an exemplary embodiment of an exemplary self-contained portable sensor system according to the present invention.

FIG. 11 depicts an exemplary embodiment of an exemplary self-contained portable sensor system 1100 according to the present invention. As illustrated, exemplary self-contained portable sensor system 1100 can include wheels 1104, power supply 1102, a communications interface 1108, transceiver 1106, MIP Controller 802; Detector System 812, and enhanced scanning solutions module 816. The exemplary self-contained portable sensor system 1100 can be modular, include redundancy and fault tolerance features such as a battery backup or generator to support the power supply 1102, is portable for ease of use in the field, and is self-contained to allow easy setup and breakdown, since minimal assembly/reassembly is required.

Figure 12A:
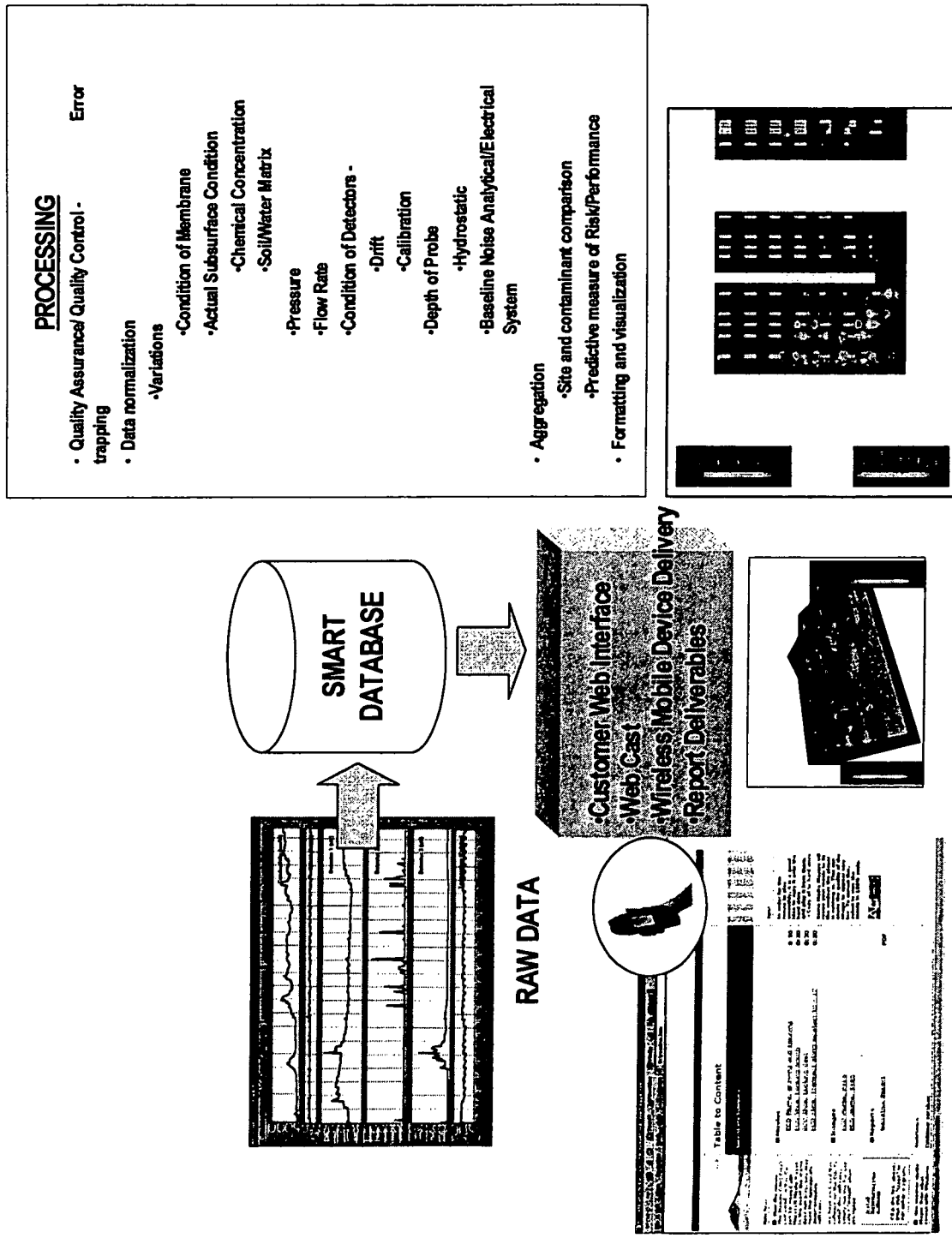
FIG. 12A depicts a diagram illustrating an exemplary embodiment of the Smart database system according to the present invention.

FIG. 12A depicts a diagram illustrating an exemplary embodiment of the Smart database system according to the present invention. As shown in the diagram, raw data can be analyzed and processed to create output such as, e.g., the depicted illustrative graphical renderings. The database can post for browser and/or wireless mobile device accessibility various reports and deliverables.

Figure 12B:
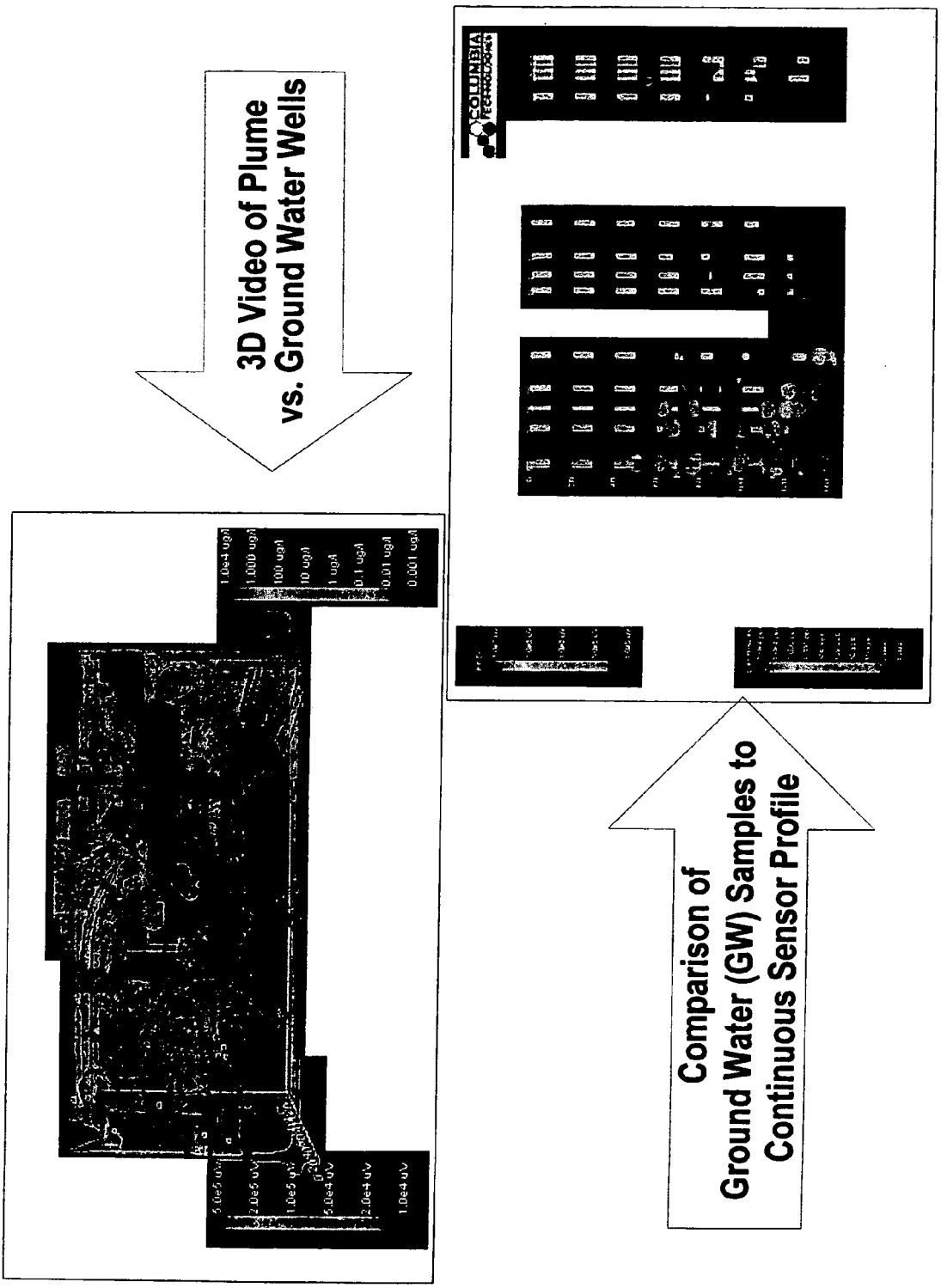
FIG. 12B depicts a diagram illustrating an exemplary embodiment of output from the Smart database system according to the present invention.

FIG. 12B depicts a diagram illustrating an exemplary embodiment of output from the Smart database system according to the present invention. The upper left diagram illustrates an exemplary 3D video of an environmental contamination site against a ground water well data set, illustrating a combination of outside data with processed data analytics visualization renderings. The lower right diagram illustrates an comparison of ground water samples to continuous sensor profile data, illustrating another combination of outside data with processed data analytics visualization renderings.

FIG. 12C depicts a graphical user interface of a browser illustrating an exemplary embodiment of a web logon window of a Demo Corporation providing access to the Smart database system according to the present invention.

FIG. 12D depicts a graphical user interface of a browser illustrating an exemplary embodiment of a web window depicting exemplary deliverables for a Manufacturing Facility of a Demo Corporation providing access to graphical renderings on the Smart database system according to the present invention.

FIG. 12E depicts a graphical user interface of a browser illustrating an exemplary embodiment of a browser window depicting exemplary selectable deliverables according to the present invention.

The exemplary embodiment of the present invention makes reference to wireless networks. A brief discussion of various exemplary wireless network technologies that could be used to implement the exemplary embodiments of the present invention now are discussed. Exemplary wireless network technology types, include, e.g., IrDA wireless technology, metropolitan area and wide area wireless networking technologies such as, e.g., MMDS, satellite, as well as various wireless short-range radio frequency (RF) technologies such as, e.g., Bluetooth, SWAP, "wireless fidelity" (Wi-Fi), IEEE std. 802.11b, IEEE 802.11a, and 802.11g, and ultrawideband (UWB). Of course any of various other wireless technologies can also be used, and it should be understood that the examples listed are not exhaustive.

IrDA is a standard method for devices to communicate using infrared light pulses as promulgated by the Infrared Data Association from which the standard gets its name. IrDA is generally the way that television remote controls operate. Since all remote controls use this standard, a remote from one manufacturer can control a device from another manufacturer. Since IrDA devices use infrared light, they depend on being in direct line of sight with each other. Although present IrDA-based networks are capable of transmitting data at speeds up to 4 megabits per second (Mbps), the requirement for line of sight means that an access point would be necessary in each office where a user would want to synchronize, limiting the usefulness of an IrDA network in some environments. Bluetooth is an example of a shortrange wireless radio frequency (RF) emerging wireless technology promising to unify several wireless technologies for use in low power radio frequency (RF) networks. Bluetooth is not expected to replace the need for high-speed data networks between computers. Bluetooth communicates on a frequency of 2.45 gigahertz, which has been set aside by international agreement for the use of industrial, scientific and medical devices (ISM).

Examples of other short-range wireless RF technology include SWAP and Wi-Fi. The SWAP and Wi-Fi specifications are based on the original Institute of Electrical and Electronics Engineers (IEEE) wireless local area network (LAN) specification, known as IEEE standard 802.11. Home radio frequency (RF) (HomeRF) developed the Shared Wireless Access Protocol (SWAP) wireless standard. Wireless Ethernet Compatibility Alliance (WECA) advocates the so-called "wireless fidelity" (Wi-Fi) which is a derivative of the IEEE std. 802.11b. The original IEEE std. 802.11 designated two ways of communicating between wireless LAN devices and allowed for speeds up to 2 Mbps. Both IEEE std. 802.11 communication methods, direct-sequence spread spectrum (DSSS) and frequency-hopping spread spectrum (FHSS), use frequency-shift keying (FSK) technology. Also, both DSSS and FHSS are based on spread-spectrum radio waves in the 2.4-gigahertz (GHz) frequency range. Home RF's SWAP combines DECT, a time division multiple access (TDMA) voice service used to support the delivery of isochronous data and a carrier sense multiple access/collision avoidance (CSMA/CA) service (derived from IEEE std. 802.11). WECA's Wi-Fi standard provides IEEE std. 802.11b standard wireless LAN compliant wireless communication technologies.

UWB is yet another short-range RF wireless communication system making use of small pulses of energy in the time domain that in the frequency domain are spread across a very wide bandwidth and are transmitted at a very low power level that is on the order of magnitude of noise. The pulses can be encoded to carry information by, e.g., differing the timing of arrival of pulses in the time domain.

IV. CONCLUSION

While various embodiments of the present invention have been described above, it should be understood that they have been presented by way of example and not limitation. It will be apparent to persons skilled in the relevant art(s) that various changes in form and detail can be made therein without departing from the spirit and scope of the invention. In fact, after reading the description herein, it will be apparent to one skilled in the relevant art(s) how to implement the invention in alternative embodiments.

What is claimed is:

1. A mobile enhanced scanning solutions module comprising:
   a flow control subsystem controlling the rate of flow of a carrier gas obtained from an environmental subsurface;
   a plurality of measurement subsystems measuring or detecting in real time at least one contaminant in said carrier gas, said plurality of measurement subsystems comprising:
      a detector subsystem coupled to said flow control subsystem,
      a moisture separator subsystem coupled to said flow control subsystem, and
      a sampling subsystem coupled to said flow control subsystem;
   wherein said flow control subsystem switches, controls valves, and controls rate of flow of said carrier gas in real time among said plurality of measurement subsystems;
   a global positioning system (GPS) receiver integrated with a mobile data acquisition system geo-referencing data acquired from at least one of said detector subsystem or said sampling subsystem; and
   a software control subsystem coupled to said plurality of measurement subsystems and said flow control subsystem, sensing conditions in real time including said measured or detected contaminant, and at least one of configuring or reconfiguring said flow control subsystem and/or combinations of said plurality of measurement subsystems in real time, prior to exhaust, including timing, sequencing, monitoring, logging or recording data, in response to said sensed conditions.

2. The enhanced scanning solutions module of claim 1, wherein said sampling subsystem comprises at least one of:
   a sample loop; an absorbent trap; or a gas chromatography injection port.

3. The enhanced scanning solutions module of claim 1, further comprising at least one of:
   an in situ gas stream; a dryer; a moisture sensor detector; a pneumatic supply; a power supply; a bypass module; a feedback signal; a detector subsystem feedback signal; a calibration material; a tracer gas; a calibration gas; or a pressure control subsystem.

4. The enhanced scanning solutions module of claim 1, further comprising:
   a feedback signal mechanism coupled from at least one of said plurality of measurement subsystems to at least said flow control subsystem, wherein said flow control subsystem is further coupled to said software control subsystem.

5. The enhanced scanning solutions module of claim 1,
   wherein said software control subsystem configures or reconfigures said plurality of measurement subsystems in response to at least one of: a measured or detected volatile organic compound or sensed hydrogeological environmental conditions, wherein said environmental subsurface comprises an area beneath at least one of a surface of earth, and/or a surface of a body of water, and
   wherein said measured or detected volatile organic compound or sensed hydrogeological environmental conditions are measured or detected from said carrier gas received from a membrane interface probe (MIP) sensor driven into said environmental subsurface and in direct contact with soil as well as at least one of ground water, and/or contaminant vapor.

6. A mobile enhanced scanning solutions module comprising:
   a plurality of measurement subsystems measuring or detecting in real time at least one contaminant from a sample from an environmental subsurface, said plurality of measurement subsystems comprising:
      a detector subsystem selectively coupled to an in situ gas stream, and
      a sampling subsystem selectively coupled to the in situ gas stream;
   a global positioning system (GPS) receiver integrated with a mobile data acquisition system geo-referencing data acquired from at least one of said detector subsystem and/or said sampling subsystem;

a software control subsystem coupled to said plurality of measurement subsystems sensing conditions in real time including at least one measured or detected contaminant and at least one of configuring or reconfiguring combinations of said plurality of measurement subsystems in real time, prior to exhaust, including timing, sequencing, monitoring, logging or recording data, in response to said sensed conditions; and wherein said environmental subsurface comprises an area beneath at least one of a surface of earth, or a surface of a body of water.

7. The enhanced scanning solutions module of claim 6, further comprising:
a moisture separator subsystem coupled to said software control subsystem, wherein said moisture separator subsystem is selectively coupled to the in situ gas stream.

8. The enhanced scanning solutions module of claim 6, wherein said sampling subsystem comprises at least one of:
a sample loop; an absorbent trap; or a gas chromatography injection port.

9. The enhanced scanning solutions module of claim 6, further comprising at least one of:
a dryer; a moisture separator; a moisture sensor detector; a pneumatic supply; a power supply; a bypass module; a feedback signal; a detector subsystem feedback signal; a calibration material; a tracer gas; a calibration gas; or a pressure control subsystem.

10. The enhanced scanning solutions module of claim 6, wherein the enhanced scanning solutions module further comprises:
an interface between said detector subsystem and a gas handling subsystem allowing insertion of at least one of: a sample, another detector, a flowpath, a flow path rate, a dryer, a moisture separator, a moisture sensor detector, a bypass, a feedback, a detector subsystem feedback, a tracer gas, a calibration gas, a calibration material, a sample loop, an absorbent trap, a gas chromatographic injection port, or a trap.

11. The enhanced scanning solutions module of claim 6, said software control subsystem comprises at least one of:
a timer; a data logger; a sequencer; a valve control system; a monitor; a display; or a recording function.

12. The enhanced scanning solutions module of claim 6, further comprising a membrane interface probe apparatus coupled to said in situ gas stream comprising:
a membrane interface probe (MIP) housing having a diameter of at least about 2.125 inches.

13. The enhanced scanning solutions module according to claim 12 wherein said MIP housing is coupled with a rod system.

14. The enhanced scanning solutions module according to claim 12 wherein said MIP housing is coupled with a push and hammer system.

15. The enhanced scanning solutions module according to claim 12 wherein said MIP housing is adapted for low sidewall support drive rod string applications.

16. The enhanced scanning solutions module according to claim 12, wherein said MIP housing comprises two or more permeable membranes.

17. The enhanced scanning solutions module of claim 6, further comprising at least one of:
a membrane interface probe (MIP) housing having two or more permeable membranes coupled to said housing; or a MIP adapted to provide circumferential sensing.

18. The enhanced scanning solutions module of claim 17, wherein said two or more permeable membranes of said MIP housing are arranged equidistant about a circumference of said MIP housing.

19. The enhanced scanning solutions module of claim 18, wherein said MIP housing provides circumferential collection of volatile organic mass by said MIP housing.

20. The enhanced scanning solutions module of claim 6, further comprising a membrane interface probe apparatus comprising:
a membrane interface probe (MIP) comprising at least one of a waterproof electrical coupling or an O-ring mechanical coupling, wherein at least one of said waterproof electrical coupling or said O-ring mechanical coupling are watertight.

21. The enhanced scanning solutions module of claim 6, further comprising a modular membrane interface probe (MIP) apparatus comprising:
a modular membrane interface probe (MIP) comprising a plurality of modular components allowing field serviceable replacement of any malfunctioning components of said plurality of modular components other than a permeable membrane and/or an entire new MIP.

22. The module of claim 21, wherein the modular MIP apparatus comprises at least one of:
an external barrel having a cavity; or
an inner core barrel assembly field-insertable into said cavity having a heater cavity, wherein said heater cavity receives a field-insertable and removable cartridge heating element.

23. The module of claim 21, wherein the modular MIP apparatus comprises a removable conductivity nose assembly.

24. The module of claim 21, wherein the modular MIP apparatus further comprises a field-insertable and removable cartridge heating element.

25. The module of claim 21, wherein the modular MIP apparatus comprises at least one of a waterproof electrical connector or an O-ring seal.

26. The module of claim 6, further comprising a membrane interface probe apparatus comprising:
a membrane interface probe (MIP) housing comprising an internal removable trap that collects and/or concentrates one or more volatile organic compounds.

27. The module of claim 26, wherein the MIP apparatus, wherein said removable trap detects concentration levels of said one or more volatile organic compounds, and specifically identifies said one or more compounds through chromatographic analysis.

28. The module of claim 26, wherein the MIP apparatus, further comprising: a calibrator that calibrates said MIP using chromatographic methods.

29. The module of claim 26, wherein the MIP apparatus further comprises means for at least one of trapping or concentrating of volatile organic compounds during at least one of MIP sampling or logging events.

30. The module of claim 6, further comprising a membrane interface probe apparatus comprising:
a membrane interface probe (MIP) comprising a heated transfer line from a body of said MIP to a surface detector suite that minimizes loss of volatile organic compounds in a cold transfer line.

31. The module of claim 6, wherein said enhanced scanning solutions module, further comprises: a sample introduction system coupled to said MIP that introduces a calibration gas; and allows for simultaneous sampling of a volatile organic gas stream for chromatographic analysis.

32. The module of claim 6, further comprising:
a depth measurement device coupled to said global positioning system (GPS) receiver integrated with said mobile data acquisition system allow simultaneous geo-referencing in at least three (3) dimensions of at least one of said detection subsystem or said sampling subsystem, in an environmental subsurface, wherein said environmental subsurface comprises an area beneath at least one of a surface of earth, or a surface of a body of water, and wherein said in situ gas stream is coupled to a moveable direct reading sensor in direct contact with at least one of soil, water or vapor.

* * * * *